US008066732B2

(12) United States Patent
Paul et al.

(10) Patent No.: US 8,066,732 B2
(45) Date of Patent: Nov. 29, 2011

(54) INVERTING OCCLUSION DEVICES, METHODS, AND SYSTEMS

(75) Inventors: Ram H. Paul, Bloomington, IN (US); Brian C. Case, Bloomington, IN (US); Jacob A. Flagle, Indianapolis, IN (US)

(73) Assignee: Cook Incorporated, Bloomington, IN (US)

( * ) Notice: Subject to any disclaimer, the term of this patent is extended or adjusted under 35 U.S.C. 154(b) by 920 days.

(21) Appl. No.: 11/322,145

(22) Filed: Dec. 29, 2005

(65) Prior Publication Data

US 2006/0149309 A1  Jul. 6, 2006

Related U.S. Application Data

(60) Provisional application No. 60/640,544, filed on Dec. 30, 2004.

(51) Int. Cl.
*A61M 29/00* (2006.01)
(52) U.S. Cl. .................. 606/195; 606/192; 606/194
(58) Field of Classification Search .......... 606/191, 606/192, 194, 195; 623/1.11, 1.12
See application file for complete search history.

(56) References Cited

U.S. PATENT DOCUMENTS

| 4,271,839 | A | * | 6/1981 | Fogarty et al. ............. 606/194 |
| 4,512,342 | A | | 4/1985 | Zaneveld et al. |
| 4,705,517 | A | | 11/1987 | DiPisa, Jr. |
| 4,819,637 | A | | 4/1989 | Dormandy, Jr. et al. |
| 4,863,440 | A | | 9/1989 | Chin |
| 4,877,028 | A | | 10/1989 | Sandhaus |
| 4,902,508 | A | | 2/1990 | Badylak et al. |
| 4,956,178 | A | | 9/1990 | Badylak et al. |
| 5,061,245 | A | | 10/1991 | Waldvogel |
| 5,222,970 | A | | 6/1993 | Reeves |
| 5,275,826 | A | | 1/1994 | Badylak et al. |
| 5,281,422 | A | | 1/1994 | Badylak et al. |
| 5,304,123 | A | | 4/1994 | Atala et al. |
| 5,330,446 | A | * | 7/1994 | Weldon et al. ............. 604/271 |
| 5,382,261 | A | | 1/1995 | Palmaz |
| 5,411,475 | A | | 5/1995 | Atala et al. |
| 5,456,693 | A | | 10/1995 | Conston et al. |
| 5,516,533 | A | | 5/1996 | Badylak et al. |
| 5,554,389 | A | | 9/1996 | Badylak et al. |
| 5,609,598 | A | | 3/1997 | Laufer et al. |

(Continued)

FOREIGN PATENT DOCUMENTS

JP   10-127754   5/1998

(Continued)

OTHER PUBLICATIONS

Gorisch et al., "Heat Induced Contraction of Blood Vessels", *Lasers in Surgery and Medicine*. 1982. vol. 2, No. 1. pp. 1-13. Wiley-Liss, United States.

(Continued)

*Primary Examiner* — Gary Jackson
*Assistant Examiner* — Michael Mendoza
(74) *Attorney, Agent, or Firm* — Woodard, Emhardt, Moriarty, McNett & Henry LLP

(57) ABSTRACT

Described are devices, methods and systems useful for achieving occlusion of vascular vessels. Percutaneous procedures can be used to occlude and obliterate the greater saphenous vein, for example in the treatment of varicose vein condition caused by venous reflux. Certain embodiments encompass the percutaneous delivery of an occlusion device inverted within a cannula, its deployment and filling, so as to occlude or obliterate a portion of a vascular vessel.

42 Claims, 23 Drawing Sheets

U.S. PATENT DOCUMENTS

| | | | |
|---|---|---|---|
| 5,611,358 | A | 3/1997 | Suval |
| 5,634,936 | A | 6/1997 | Linden et al. |
| 5,685,716 | A * | 11/1997 | Linkow .......................... 433/173 |
| 5,779,672 | A | 7/1998 | Dormandy, Jr. |
| 5,830,228 | A | 11/1998 | Knapp et al. |
| 5,925,063 | A | 7/1999 | Khosravi |
| 5,955,110 | A | 9/1999 | Patel et al. |
| 5,993,844 | A | 11/1999 | Abraham et al. |
| 6,036,687 | A | 3/2000 | Laufer et al. |
| 6,071,285 | A * | 6/2000 | Lashinski et al. ............ 623/1.11 |
| 6,096,021 | A | 8/2000 | Helm et al. |
| 6,096,052 | A | 8/2000 | Callister et al. |
| 6,099,567 | A | 8/2000 | Badylak et al. |
| 6,200,336 | B1 | 3/2001 | Pavcnik et al. |
| 6,206,907 | B1 | 3/2001 | Marino et al. |
| 6,206,931 | B1 | 3/2001 | Cook et al. |
| 6,245,090 | B1 | 6/2001 | Gilson et al. |
| 6,299,619 | B1 | 10/2001 | Greene et al. |
| 6,312,405 | B1 | 11/2001 | Meyer et al. |
| 6,436,118 | B1 * | 8/2002 | Kayan ............................ 606/192 |
| 6,444,229 | B2 | 9/2002 | Voytik-Harbin et al. |
| 6,475,232 | B1 | 11/2002 | Babbs et al. |
| 6,547,804 | B2 | 4/2003 | Porter et al. |
| 6,592,566 | B2 | 7/2003 | Kipke et al. |
| 6,666,892 | B2 | 12/2003 | Hiles et al. |
| 6,736,793 | B2 | 5/2004 | Meyer et al. |
| 6,790,220 | B2 | 9/2004 | Morris et al. |
| 2002/0010418 | A1 | 1/2002 | Lary et al. |
| 2002/0058640 | A1 | 5/2002 | Abrams et al. |
| 2003/0013989 | A1 | 1/2003 | Obermiller et al. |
| 2003/0040733 | A1 | 2/2003 | Cragg et al. |
| 2003/0051735 | A1 | 3/2003 | Pavcnik et al. |
| 2003/0060817 | A1 | 3/2003 | Sauvageau et al. |
| 2003/0153935 | A1 | 8/2003 | Mialhe |
| 2003/0229366 | A1 | 12/2003 | Reggie et al. |
| 2004/0015159 | A1 | 1/2004 | Slater et al. |
| 2004/0044351 | A1 | 3/2004 | Searle |
| 2004/0158185 | A1 | 8/2004 | Moran et al. |
| 2004/0254589 | A1 | 12/2004 | Darnis et al. |
| 2005/0113798 | A1 | 5/2005 | Slater et al. |

FOREIGN PATENT DOCUMENTS

| | | |
|---|---|---|
| WO | WO 99/30766 | 6/1999 |
| WO | WO 00/45691 | 8/2000 |
| WO | WO 01/70091 | 9/2001 |
| WO | WO 03/009764 | 2/2003 |
| WO | WO 03/043506 | 5/2003 |
| WO | WO 2004/103187 | 12/2004 |
| WO | WO 2005/020847 | 3/2005 |
| WO | WO 2005/053547 | 6/2005 |

OTHER PUBLICATIONS

Luo, J, et al. "Direct Intrahepatic Portacaval Shunt: An Experimental Study". *World Journal of Gastroenterology*. Feb. 2003. vol. 9, No. 2. pp. 324-328. The WJG Press, China.

Min, R.J., et al. "Endovenous Laser Treatment of Saphenous Vein Reflux: Long-Term Results". *Journal of Vascular and Interventional Radiology*. Aug. 2003. vol. 14, No. 8. pp. 991-996. Society of Cardiovascular and Interventional Radiology, United States.

* cited by examiner

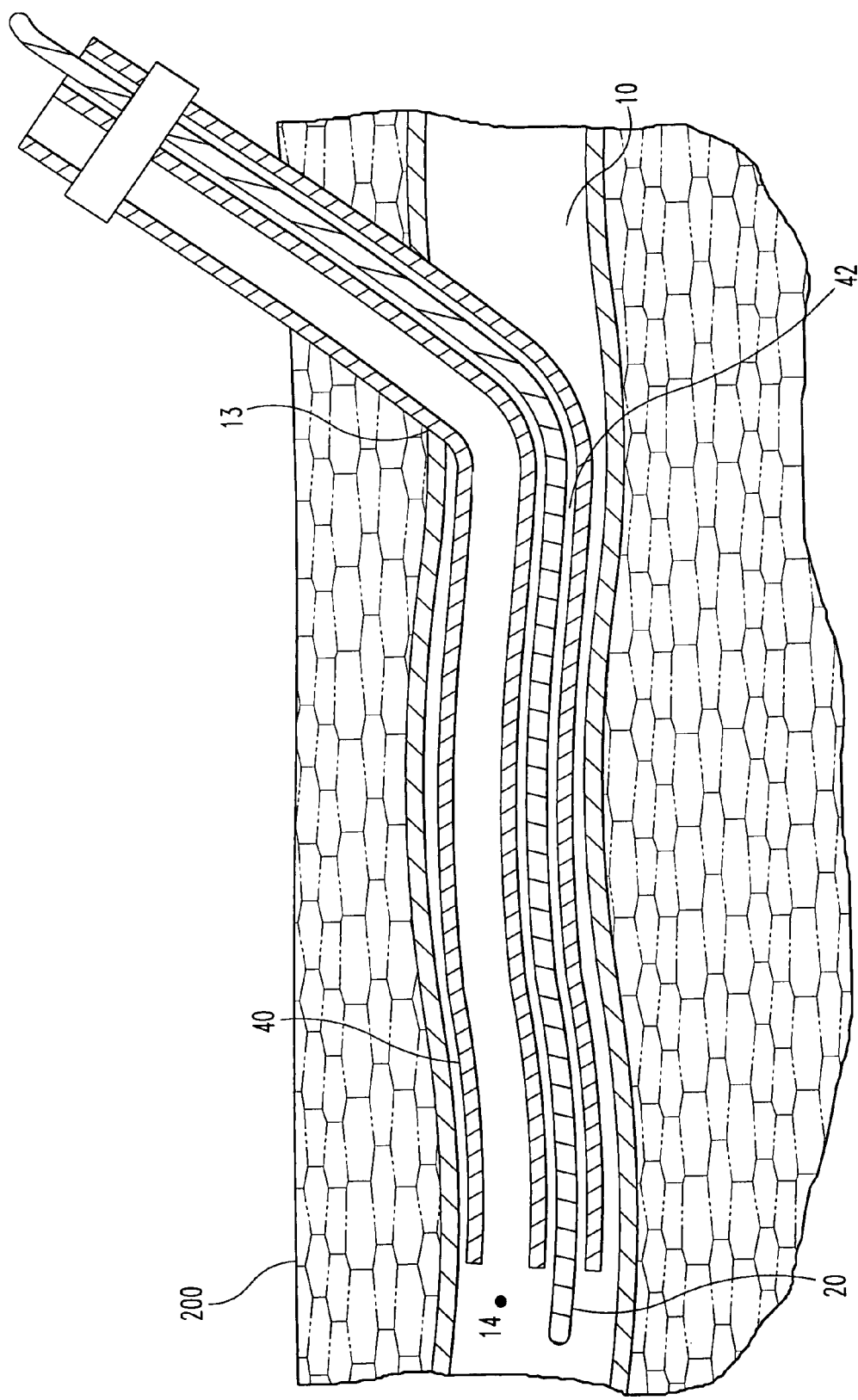

INVERTING OCCLUSION DEVICES, METHODS, AND SYSTEMS

STATEMENT OF RELATED APPLICATIONS

This application claims the benefit of priority of U.S. Provisional Patent Application Ser. No. 60/640,544 filed Dec. 30, 2004 which is incorporated herein by reference in its entirety.

BACKGROUND

The present invention resides generally in the field of devices and methods useful for the occlusion of vascular vessels, and in a particular aspect relates to the occlusion of the greater or lessor saphenous vein to treat complications, such as varicose vein condition, resultant of venous reflux.

As further background, vascular vessels are comprised of tissue and are the conduit for circulating blood through a mammalian body. A vascular vessel that carries blood from the heart is known as an artery. A vascular vessel that returns blood to the heart is known as a vein. There are three types of veins in a human: deep veins, which are located deep in the body close to the bones, superficial veins, which are located close to the skin, and perforating veins, which are smaller veins that connect the deep veins to the superficial veins.

To assist blood flow, venous vascular vessels contain venous valves. Each venous valve is located inside the vein and typically includes at least two valve leaflets, which are disposed annularly along the inside wall of the vein. These leaflets open to permit blood flow toward the heart and close, upon a change in pressure, such as a transition from systole to diastole, to restrict the back flow of blood. When blood flows towards the heart, the venous pressure forces the valve leaflets to move apart in a downstream flexing motion, thereby creating an open path for blood flow. The leaflets normally flex together when moving in the upstream direction; therefore, they return to a closed position to restrict or prevent blood flow in the upstream, or retrograde, direction after the venous pressure is relieved. The leaflets, when functioning properly, extend radially inward toward one another such that the leaflet tips, or cusps contact each other when the valve is closed.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood will collect, or pool in vessels beneath the valve. This pooling of blood causes an increase in the venous pressure below the valve. Venous valves that allow such deleterious retrograde flow are known as incompetent or inadequate venous valves. The condition resulting from such incompetent venous valves is known as venous valve insufficiency.

In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

A common method of treatment for venous valve insufficiency is the placement of an elastic stocking around the patient's leg to apply external pressure to the vein, forcing the walls radially inward to force the leaflets into apposition. Although sometimes successful, the tight stocking is quite uncomfortable, especially in warm weather, because the stocking must be constantly worn to keep the leaflets in apposition. The elastic stocking also affects the patient's physical appearance, thereby potentially having an adverse psychological affect. This physical and/or psychological discomfort can lead to the patient removing the stocking, thereby inhibiting treatment.

Surgical methods for treatment of venous valve insufficiency have also been developed. A vein with incompetent venous valves can be surgically constricted to bring incompetent leaflets into closer proximity in hopes of restoring natural valve function. Methods for surgical constriction of an incompetent vein include implanting a frame around the outside of the vessel, placing a constricting suture around the vessel (e.g., valvuloplasty), or other types of treatment to the outside of the vessel to induce vessel contraction. Other surgical venous valve insufficiency treatment methods include bypassing or replacing damaged venous valves with autologous sections of veins containing competent valves.

Another surgical method includes vein stripping and ligation. In this procedure, the femoral vein and other major venous tributaries are disconnected from the greater saphenous vein (GSV) and tied off. Next, the GSV is removed from the leg by advancing a wire through the vein, tying the wire to a saphenous vein end, and then pulling the wire, and vein, out through an incision in the upper calf or ankle. Unfortunately, the above surgeries require at least one incision and have several undesirable side effects and risks, such as a long patient recovery time, the potential for scarring, and numerous other risks inherent with surgery, such as those associated with the administration of anesthesia.

Recently, various implantable prosthetic devices and minimally invasive methods for implantation of these devices have been suggested to treat venous valve insufficiency. Such prosthetic devices can be inserted intravascularly, for example from an implantation catheter. Prosthetic devices can function as a replacement venous valve, or enhance venous valve function by bringing incompetent valve leaflets into closer proximity. In one procedure, venous valve function can be enhanced by clipping the valve leaflets together with a clip made from a biocompatible material, such as a metal, polymer, or fabric. In other procedures, venous valve leaflets can be attached using a plastic or metal staple.

Recently, a number of methods have been suggested to treat varicose veins and venous valve leaflets with energy sources, such as radiofrequency (RF) energy. In one such method, valve leaflets can be fastened together with electrodes delivering RF energy. In another such method, a catheter having an electrode tip can be used to apply RF energy to cause localized heating and corresponding shrinkage of venous tissue. After treatment of one venous section is complete, the catheter can be repositioned to treat a different venous section.

Methods for treatment of varicose veins have also been developed involving various forms of sclerotherapy. Generally, sclerotherapy involves the delivery of sclerosing agents to the lumen of a vein, which induce the vein to collapse and the venous walls to fuse, thereby closing the vein.

In view of this background, the need remains for improved and alternative techniques, devices and systems for affecting bodily lumens such as vascular vessels, and in certain aspects for affecting the venous system to treat venous conditions. The present invention is addressed to these needs.

SUMMARY OF THE INVENTION

In one aspect, the present invention provides a method for treating venous reflux that includes the occlusion of a vein with an occlusion device deployed from an inverted position. In one embodiment, this method includes the deployment of an expandable occlusion device that is inverted within a cannulated delivery device at a suitable venous location. Additionally, this invention provides a method that includes locating an expandable balloon, a portion of which is inverted into the lumen of a cannulated device during delivery, in a portion of the vasculature in a manner that occludes the vasculature.

In another aspect, the invention provides a method for treating a venous dysfunction in the leg of a patient. This method includes percutaneously delivering into a venous vessel an inflatable occlusion device which is at least partially received within a cannulated device and passing fill material into the occlusion device so as to occlude the venous vessel.

In another aspect, the invention provides a method for occluding a vascular vessel or similar bodily lumen that includes locating a cannulated device and an inverted balloon that includes a remodelable material into a vascular vessel. In this method, a lumen of the cannulated device is in communication with the interior of the balloon, and the balloon is at least partially inverted prior to deployment, for instance in one embodiment having a closed balloon end received within the device lumen. Upon delivery into a vascular vessel, fill material is passed into the balloon. Advantageous such remodelable materials include extracellular matrix (ECM) material, such as small intestine submucosa. The remodelable material can be incorporated so as to provide a structural wall of the balloon.

In another aspect, the invention provides a method for treating a venous dysfunction in a leg of a human. This method includes the percutaneous delivery to a location within a saphenous vein of an at least partially inverted fillable member that is in communication with a lumen of a device. After delivery, the fillable member is deployed into the vein and is expanded using any suitable fill material. The fillable member can comprise an ECM material that is expanded using remodelable materials, such as collagenous foams and fluidized remodelable ECM materials. Additionally, the fill material can be added to the fillable member on more than one occasion, if necessary or desirable.

In another aspect, the invention provides a method for occluding a portion of the vasculature comprising the deployment of a balloon from an inverted position and the passage of fill material through a lumen of a cannulated device and into the balloon.

In another aspect, the invention provides a method for delivering a balloon to a site in a vascular vessel, wherein the balloon is deployed from at least a partially inverted position after it is located within the vessel.

In another aspect, the invention provides a medical product for occluding a vascular vessel. The medical product includes an at least partially inverted balloon, wherein the balloon is in communication with a lumen of a cannulated device.

In another aspect, the invention includes a medical assembly for occluding the vasculature. This assembly includes a cannulated device, wherein an end of the cannulated device is attached to a balloon end and at least a portion of the balloon is received within the cannulated device.

In another aspect, the invention includes a method for increasing the packing density of a balloon. This method includes folding the balloon in a controlled fashion, so as to reduce the diameter of a percutaneous balloon delivery system.

In another aspect, the invention provides a medical product that includes a vascular occlusion kit enclosed in sterile packaging. In certain aspects, the kit includes an inverted elongate occlusion device and a cannulated device.

In another aspect, the present invention provides a medical device that includes a balloon, wherein at least a portion of the balloon occupies an inverted position.

In another aspect, the present invention provides a medical product that includes an elongate occlusion device having a proximal end and a distal end. At least a portion of the elongate occlusion device is inverted.

In another aspect, the present invention provides a method for closing a vascular vessel that includes providing a fillable member, a portion of which is in an inverted configuration. Access is established to a vascular vessel with a cannulated device and at least a portion of the fillable member is located within the vascular vessel by passing the member through the cannulated lumen.

The present invention provides alternative or improved methods, systems and devices for occluding vascular and other bodily vessels. Additional embodiments as well as features and advantages of the invention will be apparent from the further descriptions herein.

BRIEF DESCRIPTION OF THE DRAWINGS

FIG. 12 depicts an illustrative deployment embodiment of the invention in that portion of the human leg occurring generally between points 13 and 14 in FIG. 1.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, certain embodiments of the present invention provide methods, devices and systems for achieving occlusion of a vascular vessel, such as a saphenous vein. Methods of the invention can be performed, for instance, in order to treat venous reflux through the greater saphenous vein (GSV) such as that involved in the varicose vein condition.

Figure 1:
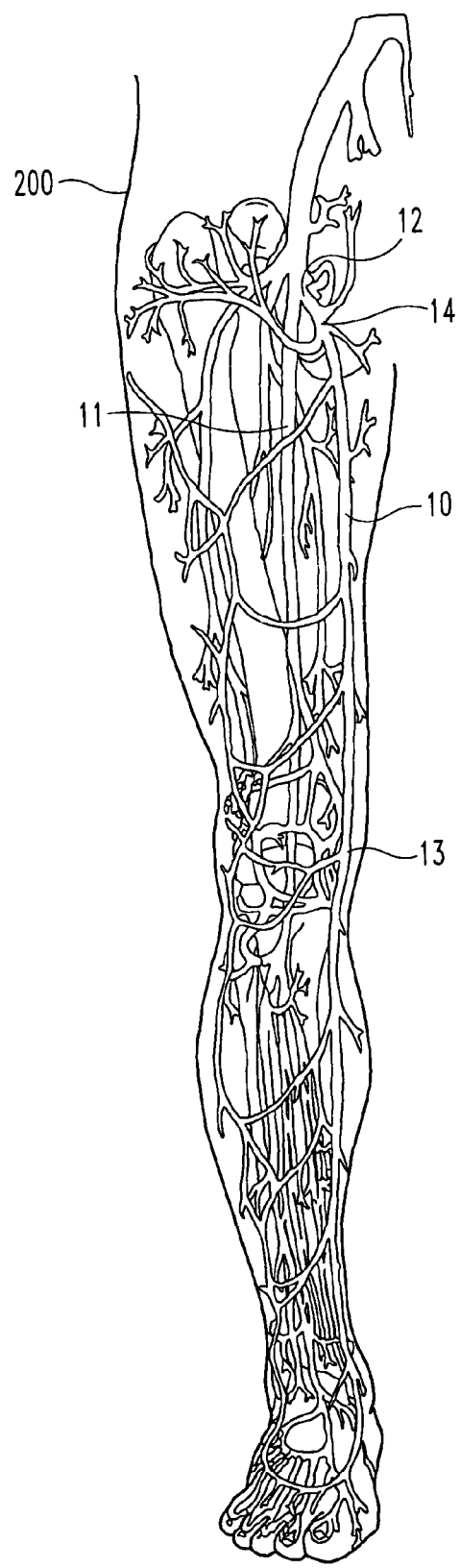
FIG. 1 depicts a human leg showing certain venous structures therein.
Figure 2:
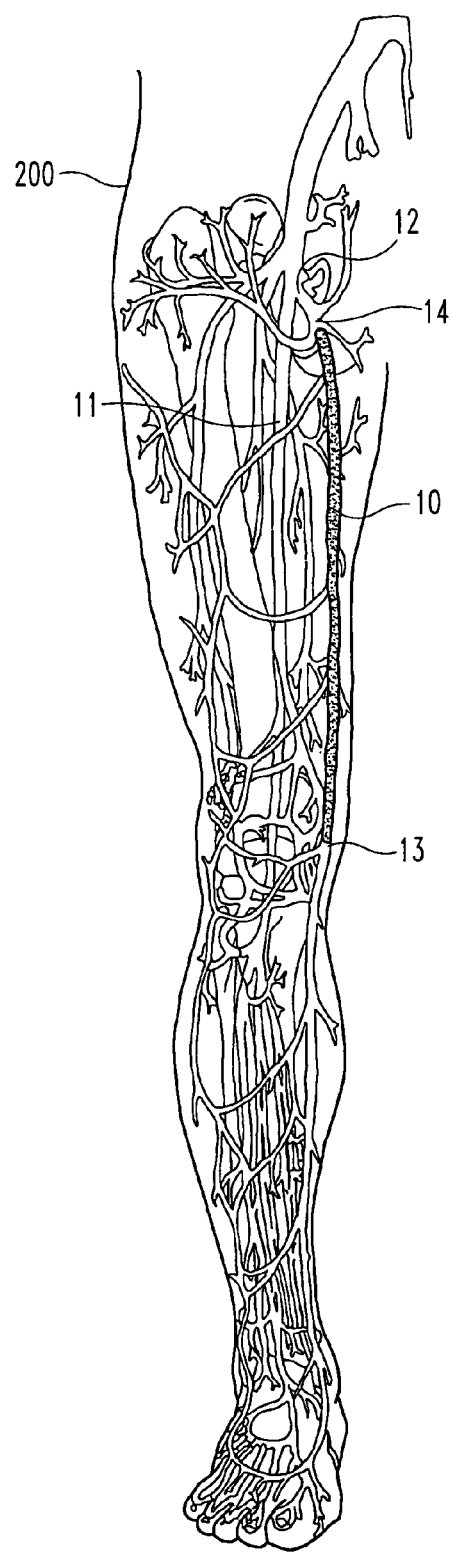
FIG. 2 depicts a human leg showing certain venous structures therein.

With reference now more particularly to the figures, shown in FIG. 1 is a diagram of a human leg 200 showing certain venous structures therein. In particular, shown is human leg 200 having GSV 10 and femoral vein 11 which adjoin at the sapheno-femoral junction 12. In accordance with certain aspects of the present invention, the GSV 10 can be occluded in a region constituting substantially all of the passage between a point 13 occurring near the medial side of the knee to a point 14 occurring prior to the sapheno-femoral junction 12, as illustrated by the shaded area in FIG. 2. Desirably, such occlusion is effective to prevent reflux of venous blood from the sapheno-femoral junction 12 in a direction down toward the medial side of the knee (e.g. at point 13). Such occlusion is effective to treat varicosities that commonly occur in lower portions of the leg, e.g. portions occurring below the knee.

Figure 3:
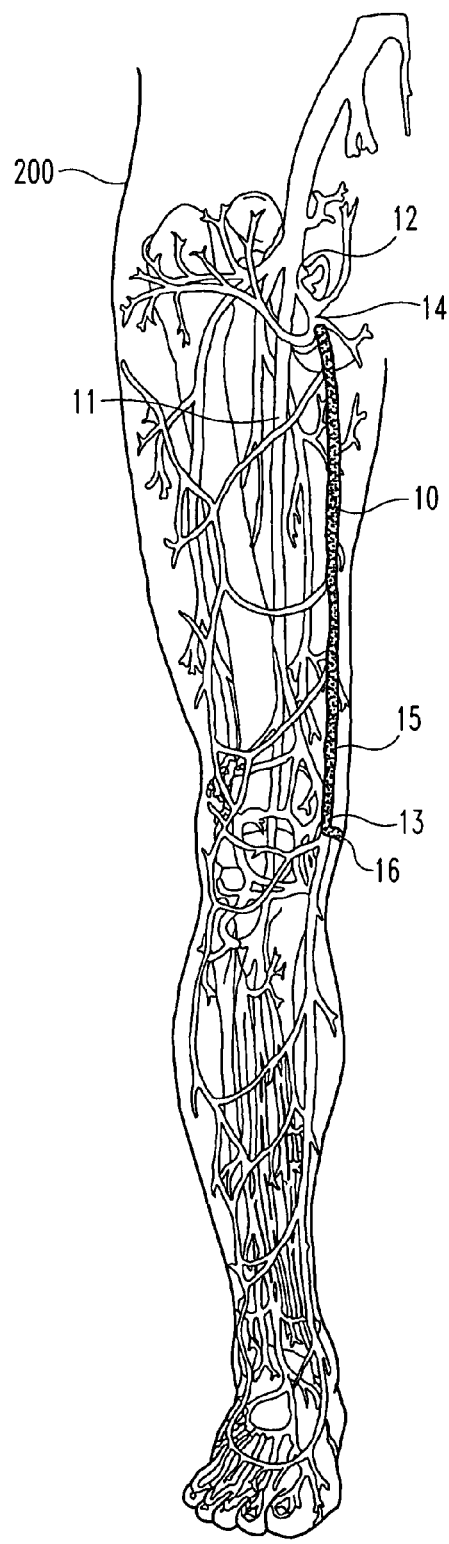
FIG. 3 depicts a human leg showing certain venous structures therein.

With reference now to FIG. 3, in certain forms of the invention, occlusion of the passage of the greater saphenous vein (GSV) occurring between points 13 and 14 is achieved by an elongate inflatable occlusion device 15 that extends from point 13 to point 14, and that may include an end portion 16 that traverses the wall of the GSV 10. This may be achieved by deploying an inflatable occlusion device 15, such as a single or double walled balloon, from an inverted position, such as where at least a portion of the balloon's exterior is exposed as an interior surface and at least a portion of the balloon's interior is exposed as an exterior surface, during a percutaneous procedure, e.g. as described hereinbelow. Additionally, the occlusion device 15 can comprise a remodelable material inflated with remodelable fill material, such that the patient's tissue remodels the device and fill material to enhance occlusion of the GSV.

Figure 4:
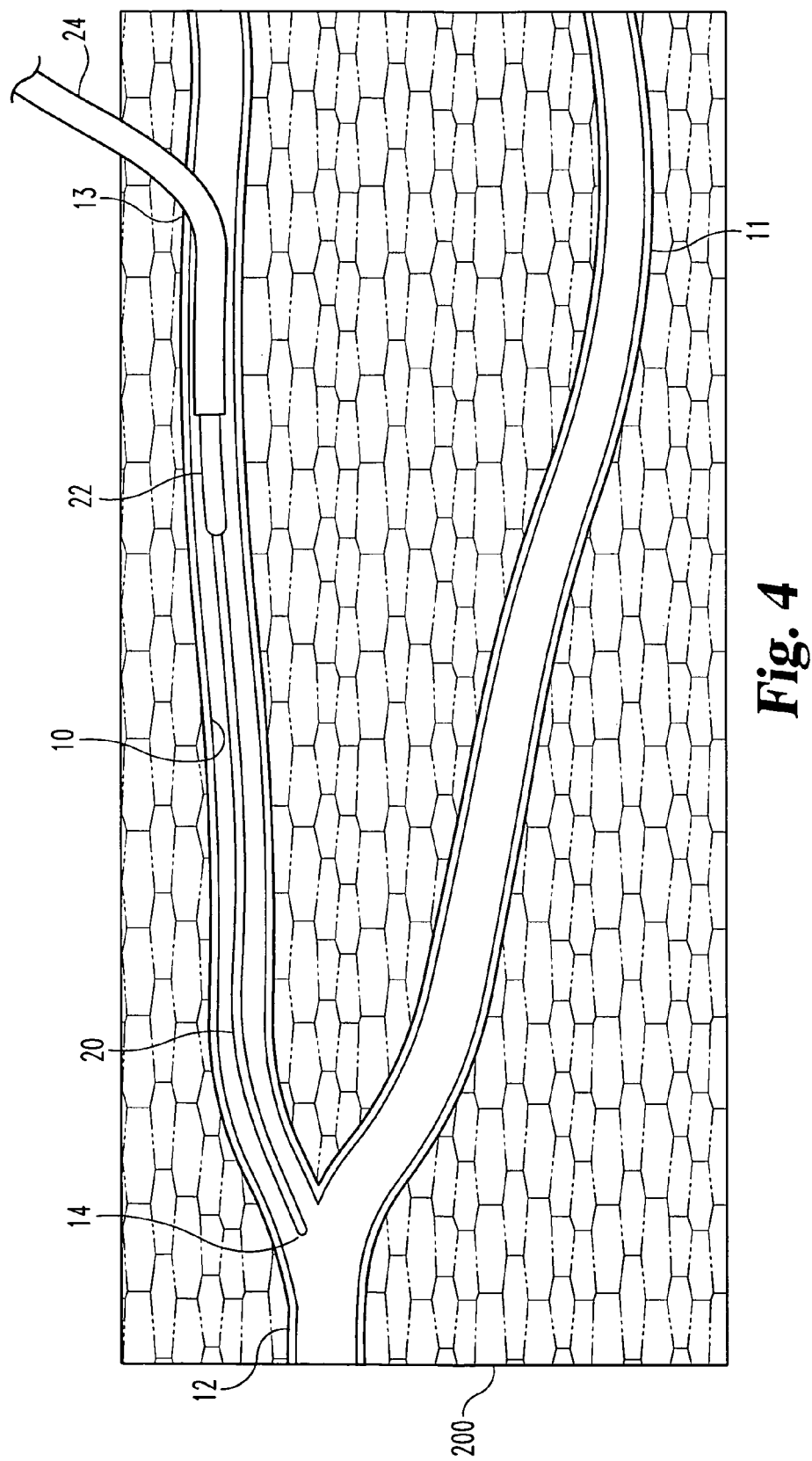
FIG. 4 depicts an illustrative deployment embodiment of the invention in that portion of the human leg occurring generally between points 13 and 14 in FIG. 1.

With reference now to FIG. 4, shown is an enlarged view of that portion of the human leg occurring generally between points 13 and 14 of FIG. 1. In an illustrative deployment procedure, percutaneous access to the GSV 10 can be achieved at point 13 using the Seldinger or any other suitable technique. For instance, an access needle (not shown) can be passed through the skin to access the GSV 10, and a wire guide 20 can be passed through the access needle and into the vein 10. Prior to deployment of an inverted occlusion device (not shown), wire guide 20 can be used for any number of conventional procedures including catheterization and imaging procedures in order to locate the sapheno-femoral junction 12. After any such preliminary procedures that are performed, the wire guide 20 can be used in a deployment procedure for an inflatable occlusion device.

Specifically, referring still to the illustrative embodiment shown in FIG. 4, a deployment sheath 24 can be placed at a suitable location in the GSV 10 using a flexible guide catheter 22, or, alternatively, a suitable dilator or dilator tip mounted on the guide catheter. In placing the sheath 24, the guide catheter 22 can be first received over the wire guide 20, then pushed into the GSV 10, where it follows along the wire guide 20 to a location within the GSV 10. Next, the sheath 24 can be received over the guide catheter 22, pushed into the GSV 10, and follow the guide catheter 22 to a suitable location in proximity to point 14. Alternatively, the sheath 24 and guide catheter 22 can be placed within the GSV 10, with the guide catheter 22 leading the sheath 24, and both can be pushed along the wire guide 20 until the sheath 24 is in a suitable location. Still alternatively, a steerable catheter can be used in conjunction with a sheath, thereby negating the need for a wire guide.

Figure 5:
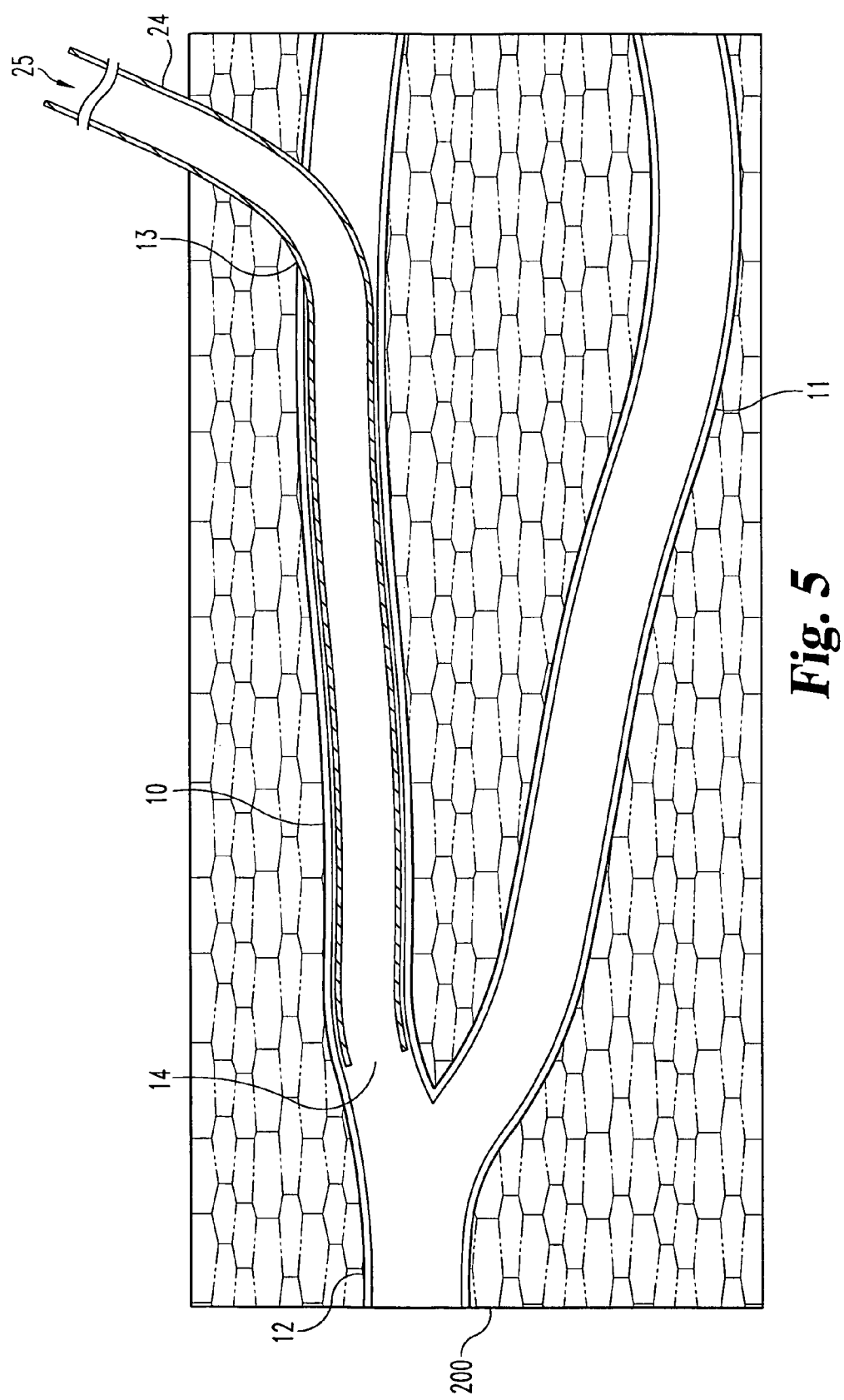
FIG. 5 depicts an illustrative deployment embodiment of the invention in that portion of the human leg occurring generally between points 13 and 14 in FIG. 1.

With reference now to FIG. 5, shown is a deployment sheath 24 received within the GSV 10 from point 13 to point 14. The guide catheter 22 and wire guide 20 have been removed from the GSV 10, leaving the sheath 24 in place with an empty lumen 25 for slidably receiving an inverted inflatable occlusion device.

Figure 6:
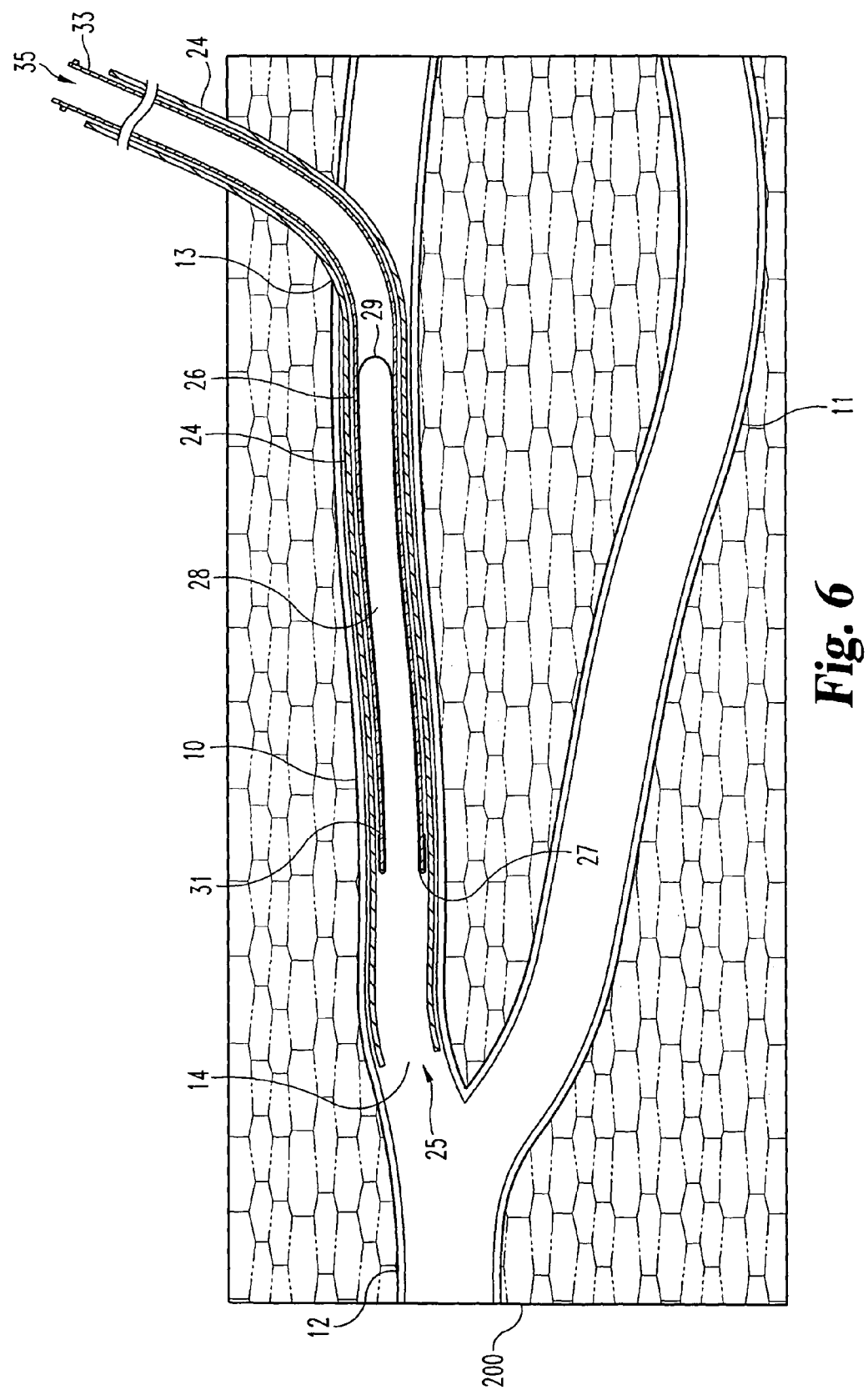
FIG. 6 depicts an illustrative deployment embodiment of the invention occurring in that portion of the human leg occurring generally between points 13 and 14 in FIG. 1.

With reference now to FIGS. 6 through 10, shown is an illustrative deployment procedure of the invention. Turning now to FIG. 6, shown is a cross-sectional view of an illustrative expandable occlusion device 28 delivery to a location within the GSV 10 where the device 28 is inverted within a delivery cannula 26. As depicted in FIG. 6, the occlusion device 28 can have a single wall, an open proximal end 27, and a closed distal end 29. The proximal end 27 of the device 28 can be secured to the distal end 31 of the cannula 26 using any suitable securing means, such as a bonding agent and/or a glue, fusion bonding, e.g. with an energy source, such as radiofrequency (RF) energy, or any suitable mechanical means, such as a compression force, e.g. a compression ring, or one or more sutures and/or staples, or the like. The proximal end 27 of the occlusion device 28 can be secured to any suitable location on the cannula's 26 distal end 31, externally or within the cannula's lumen 35.

After securing the proximal device end 27 to the cannula 26, the distal end 29 of the occlusion device 28 can be located within the lumen 35 of the cannulated device using any suitable means, such as evacuating the cannula's 26 lumen 35 with a vacuum source and/or the use of any suitable mechanical means, such as using a pusher to invert the occlusion device 28 and/or the use of gravity and/or positive pressure. In an alternative embodiment, for example, the occlusion device 28 and its distal end 29 can be located within the lumen 35 of the cannula 26 before the proximal end 27 of the occlusion device 28 is secured to the distal end 31 of the cannula 26. Still alternatively, in another embodiment, only a portion or segment of the occlusion device 28 can be inverted into the lumen 35 of the cannula 26, thereby leaving a portion of the device 28, such as the device distal end 29, containing, for example, a suitable detection means, such as a radiopaque marker (discussed in more detail below), outside the lumen of the cannula 26 to assist in locating the device 28 within the GSV 10.

Figure 7:
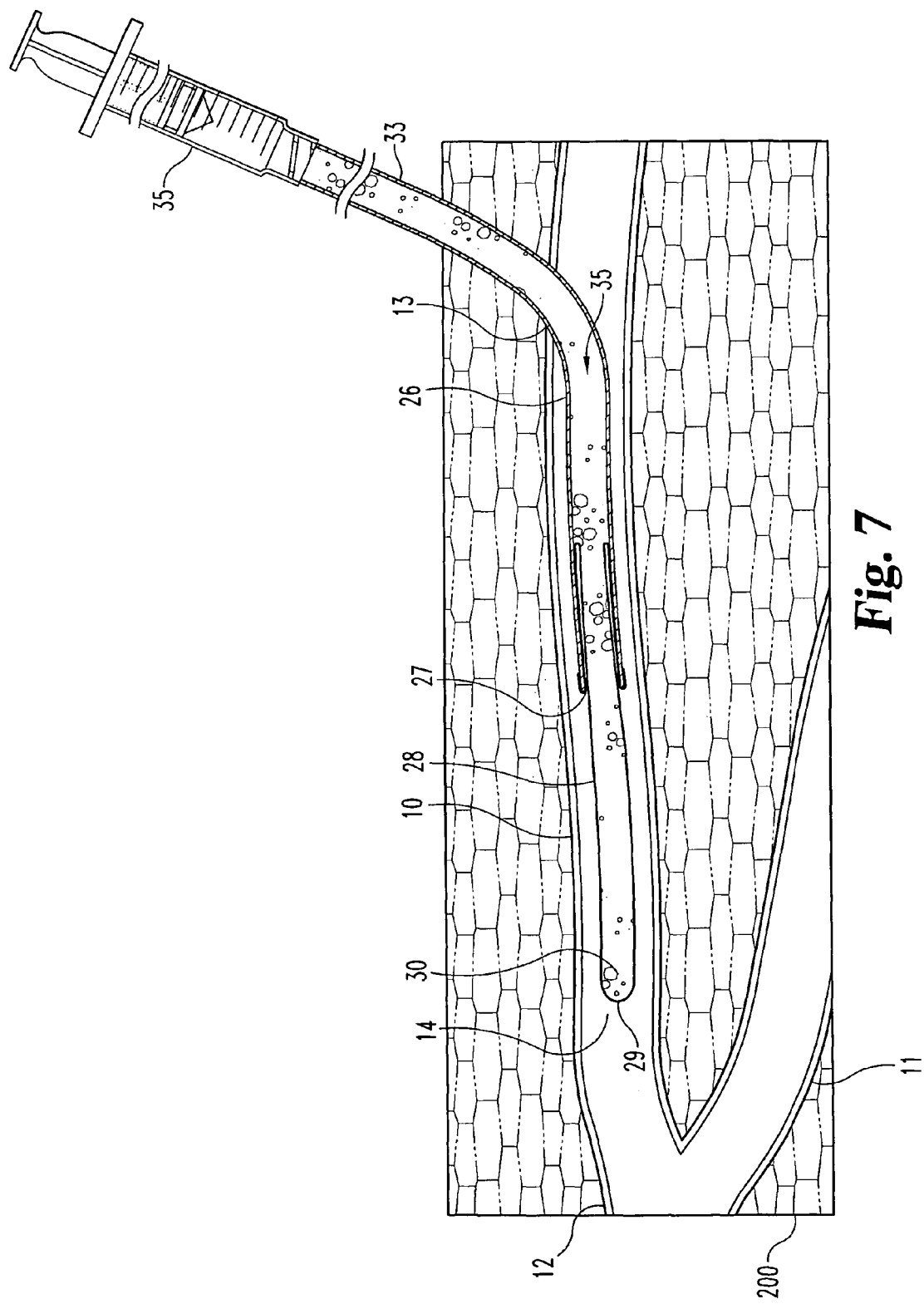
FIG. 7 depicts an illustrative deployment embodiment of the invention in that portion of the human leg occurring generally between points 13 and 14 in FIG. 1.

Continuing with the illustrative deployment embodiment, after the occlusion device 28 is located within the cannula 26, the cannula 26 can be positioned within the deployment sheath 24 and then pushed to a location within the GSV 10, leaving the proximal end of the cannula 33 external to the patient's leg 200 (see FIG. 6). Next, as depicted in FIG. 7, the deployment sheath 24 can then be retracted from the GSV 10 by holding the cannula 26 in place while pulling the sheath 24 in a proximal direction, thereby leaving the cannula 26 and occlusion device 28 in place within the GSV 10.

Next, a syringe 35 containing fill material 30 can be connected to the proximal end of the cannula 33 using any suitable fixation means, such as a luer lock connection or the like. As fill material is injected into the lumen 35 of the cannula 26, as shown in FIG. 7, the inflatable occlusion device 28 will begin to deploy or evert from the cannula's lumen 35 into the GSV 10. If necessary, to facilitate device 28 placement for example, the device 28 can be retracted toward or into the lumen 35 of the cannula by removing fill material from the device, such as through the cannula's lumen using the syringe 35. As the occlusion device 28 fully deploys from the lumen 35 of the cannula 26, the distal end 29 of the device 28 may extend beyond the sapheno-femoral junction 12 (not depicted).

Figure 8:
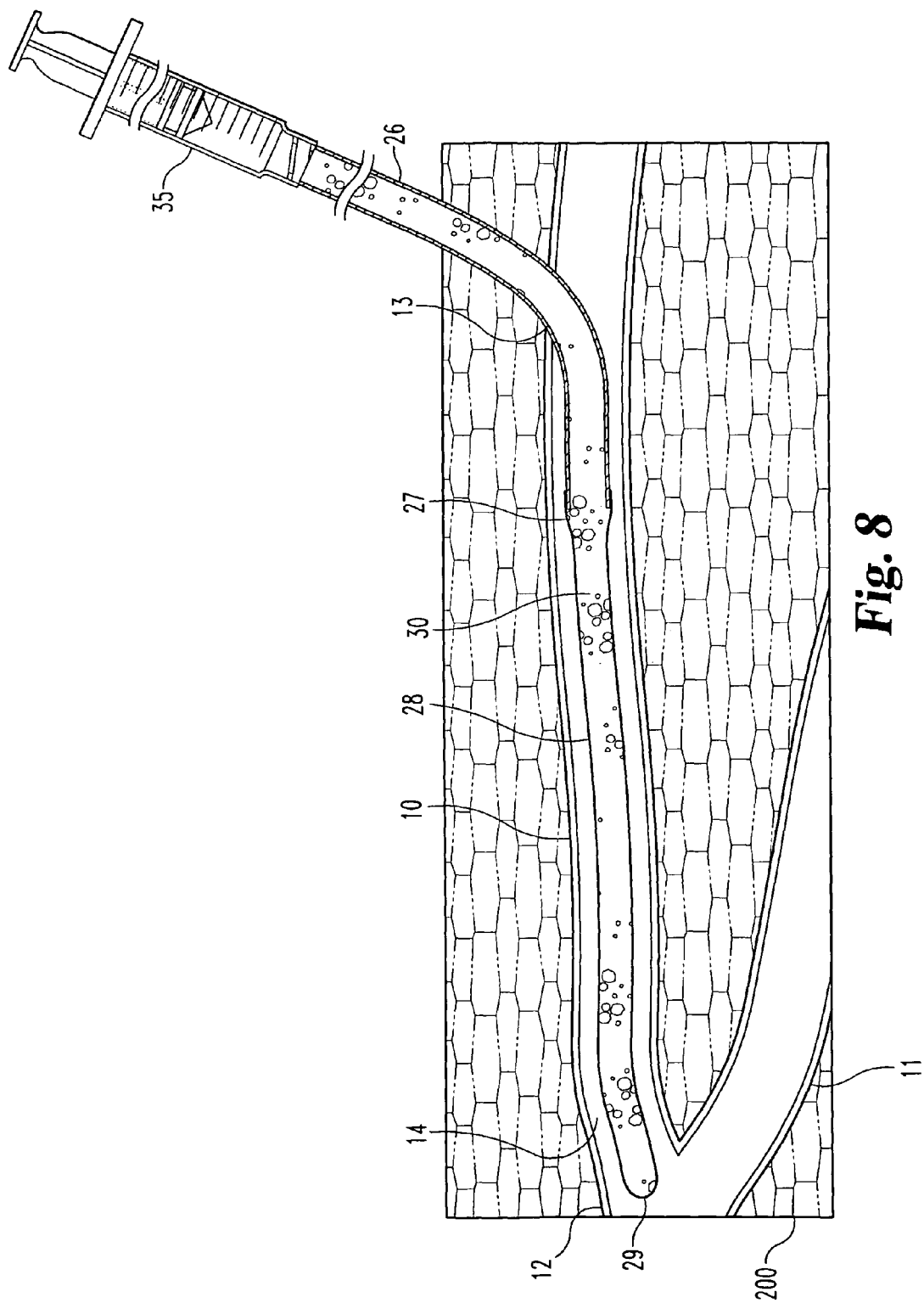
FIG. 8 depicts an illustrative deployment embodiment of the invention in that portion of the human leg occurring generally between points 13 and 14 in FIG. 1.
Figure 9:
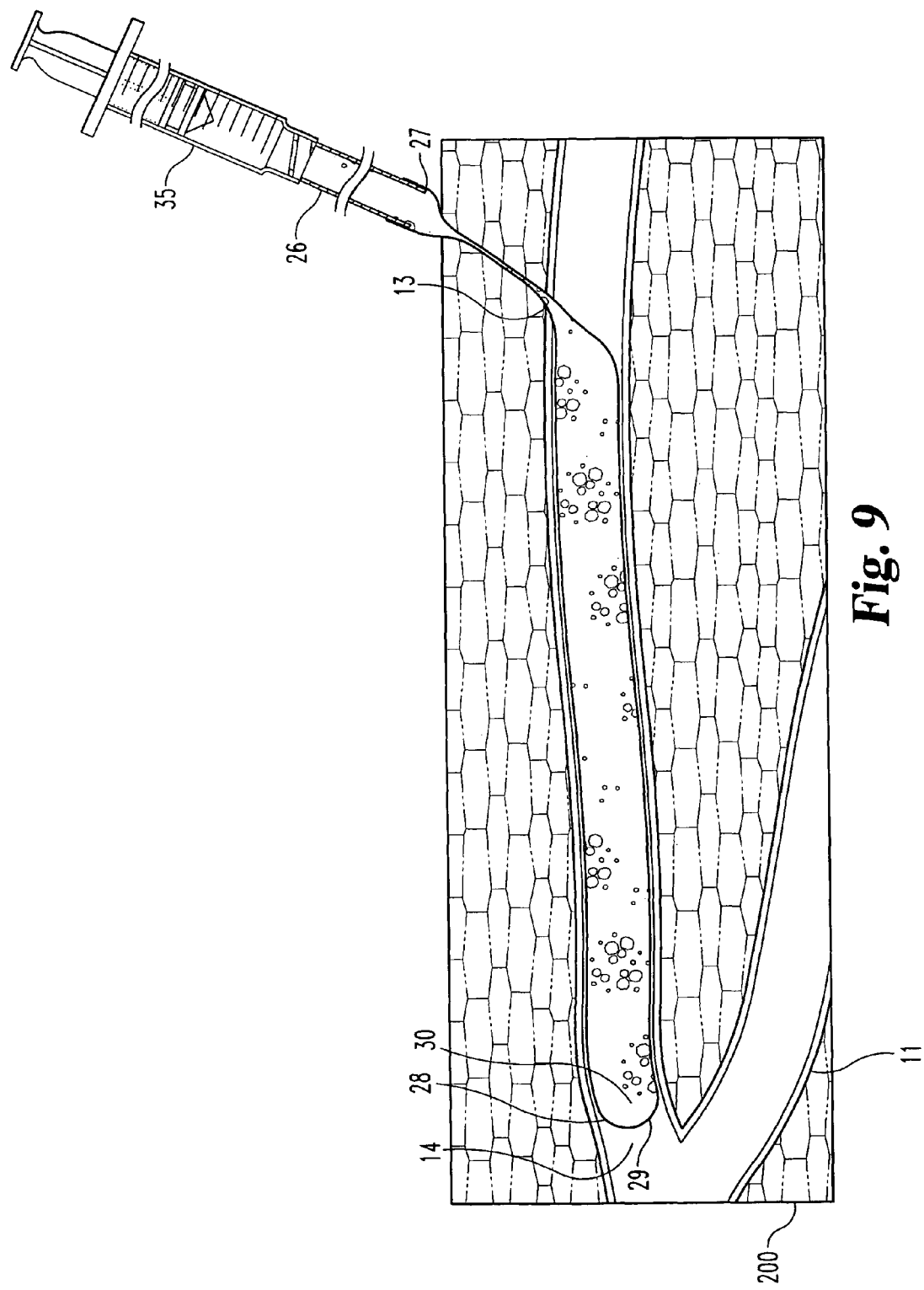
FIG. 9 depicts an illustrative deployment embodiment of the invention in that portion of the human leg occurring generally between points 13 and 14 in FIG. 1.

With reference now to FIG. 8, after the device 28 is substantially deployed, the cannula 26 can be pulled in a proximal direction in order to position the distal end 29 of the occlusion device 28 near point 14 in the GSV 10 and position the proximal end 27 of the device 28 external to the patient's body 200. Turning now to FIG. 9, after the distal end of the cannula 26 is located exterior to the body 200, and the proximal device end 29 is in a suitable location, additional fill material 30 can be added to the device 28 in order to expand the occlusion device 28 to a necessary cross-sectional diameter, such that the device 28 sufficiently prevents the reflux of blood from the iliac and femoral veins into the lower saphenous vein (LSV). The amount of reflux can be determined using any suitable method in the art, such as sonographic and/or ultrasonic imaging.

Figure 10:
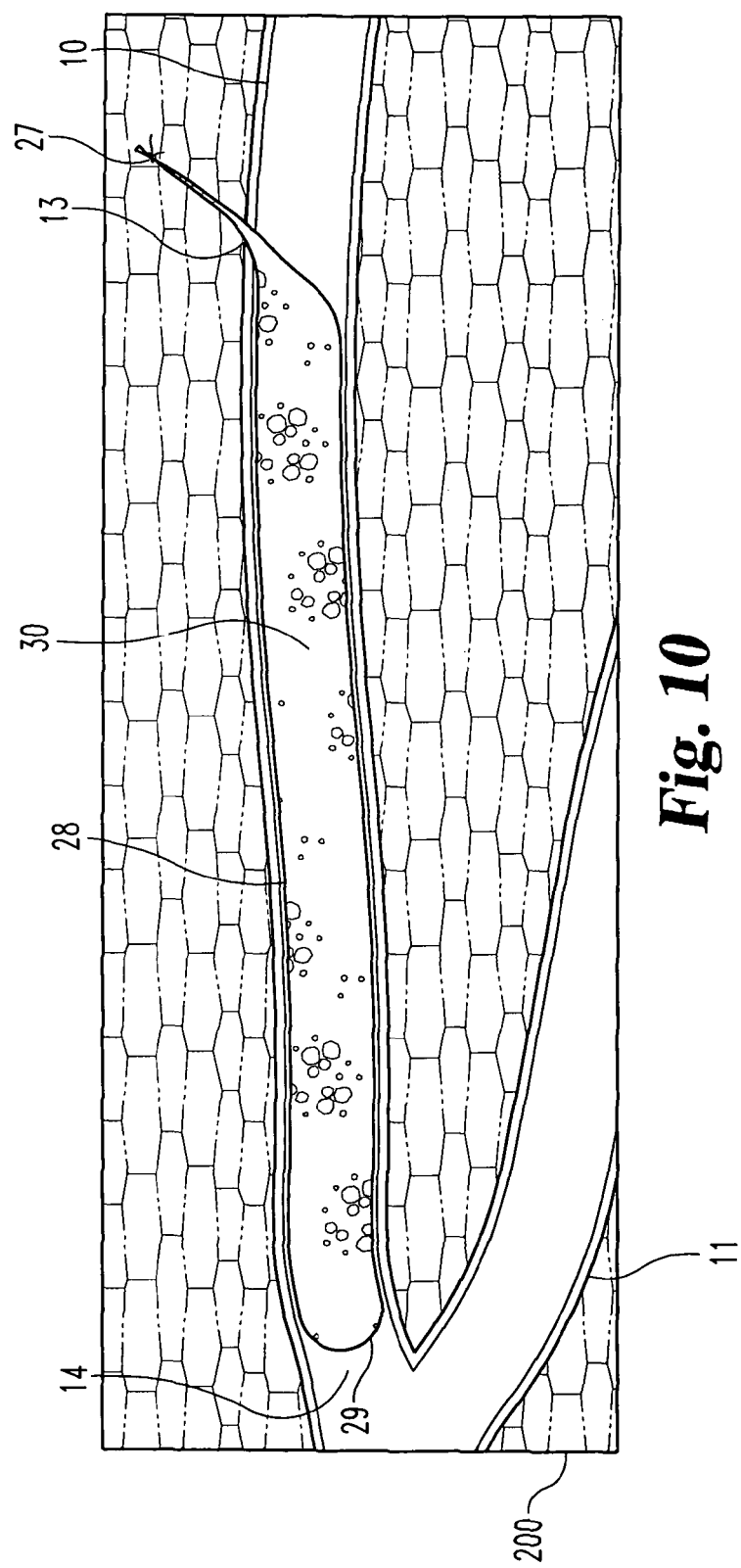
FIG. 10 depicts an illustrative deployment embodiment of the invention in that portion of the human leg occurring generally between points 13 and 14 in FIG. 1.

After the expandable occluder 28 is filled with an adequate amount of fill material 30, the proximal end of the occluder 27 can be detached from the cannula 26, trimmed, if necessary, closed, and optionally anchored. As shown in FIGS. 10 and 11B, the proximal end of the occluder 27 can be located, by trimming if necessary, to a number of suitable locations, such as a location within the GSV 10, as shown in FIG. 11B, a location external to the GSV, such as within a dermal layer of the leg 200 (FIGS. 9-10), or to a location above the leg's 200 epidermal layer (not shown). The proximal end 27 of the device can be closed using any suitable closing device or technique, such as any suitable combination of sutures (FIG. 10), staples, clamps, clips, elastic cuffs (FIGS. 11A-11B), ties, fusion bonding, or by tying the proximal end of the device into one or more knots.

Figure 11A:
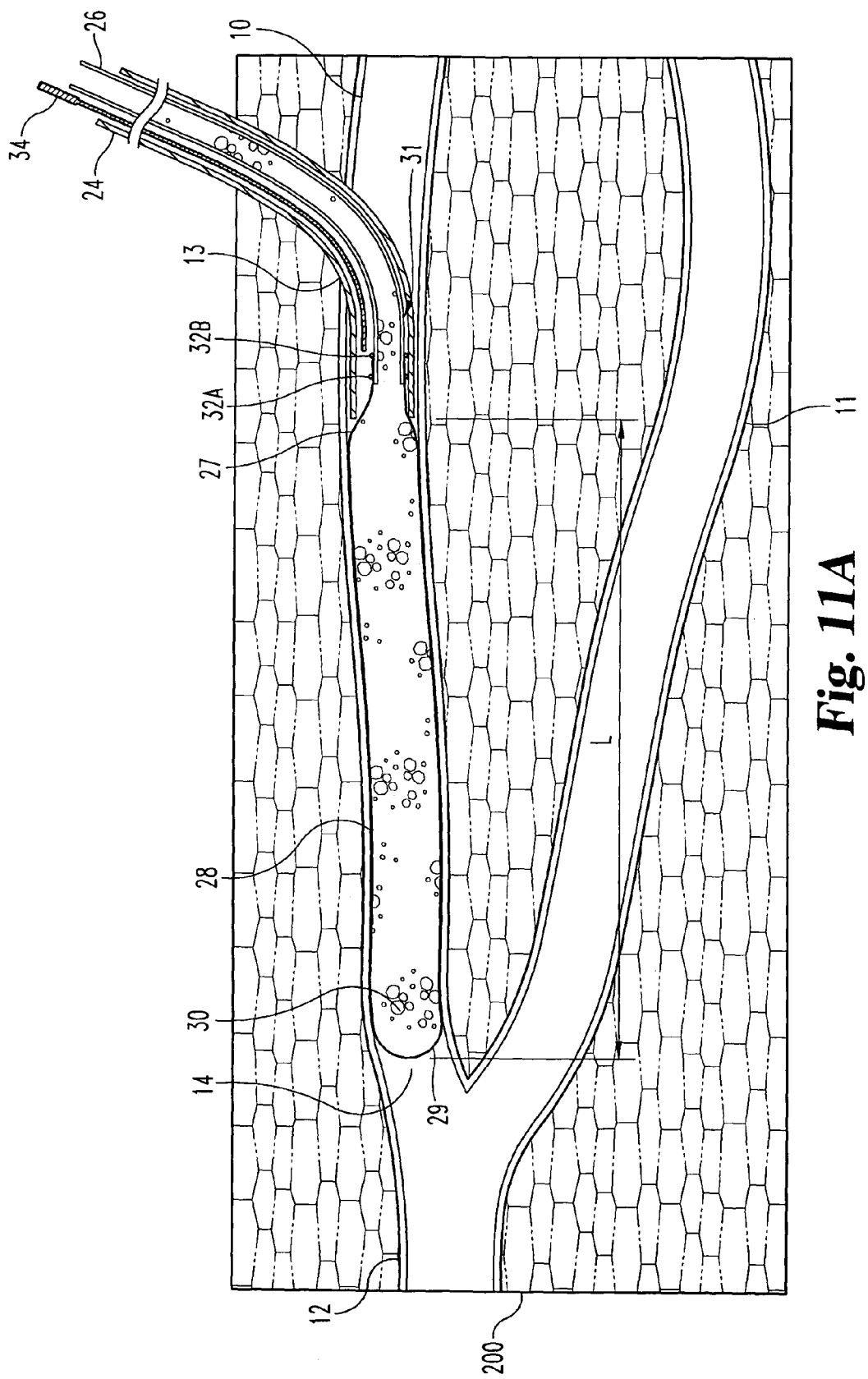
FIG. 11A depicts an illustrative deployment embodiment of the invention in that portion of the human leg occurring generally between points 13 and 14 in FIG. 1.
Figure 11B:
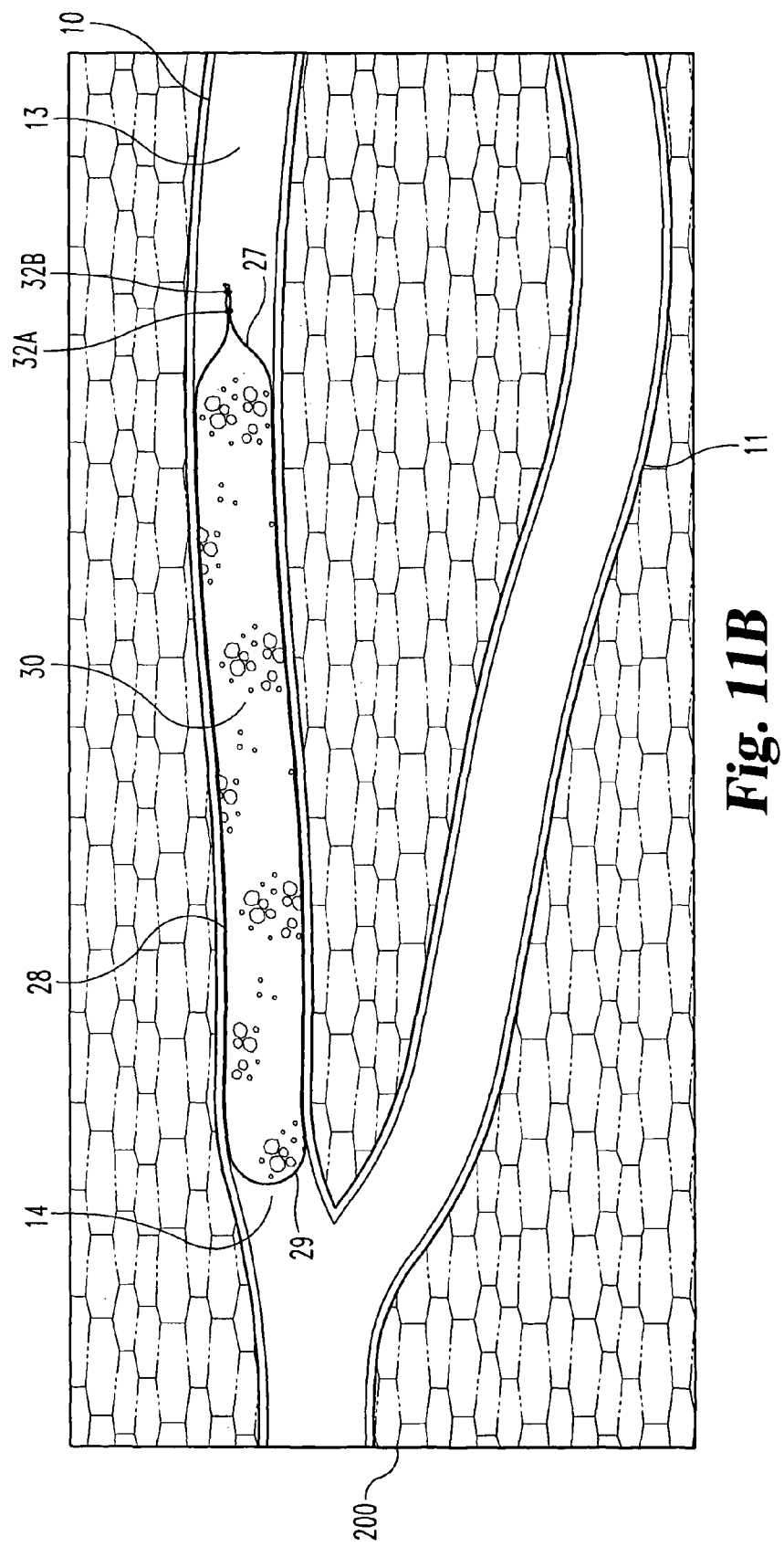
FIG. 11B depicts an illustrative deployment embodiment of the invention in that portion of the human leg occurring generally between points 13 and 14 in FIG. 1.

Turning now to another illustrative deployment embodiment, depicted in FIGS. 11A and 11B, the proximal end 27 of an inflated device 28 can be sealed within the GSV 10 using two elastic cuffs 32A, 32B. When sealing the proximal end 27 of a device 28 within the GSV 10, for example, the length "L" of the elongate occlusion device 28 can be selected so that the distal end 29 of the device 28 is located proximate to point 14 (and the sapheno-femoral junction 12) when the proximal end 27 of the device 28 is located proximate point 13 within the GSV 10.

With reference to FIG. 11A, an illustrative deployment embodiment can include delivering an inverted balloon 28 into the GSV 10 through a sheath 24 while leaving the sheath 24 in place within the GSV 10 during the deployment and inflation of the balloon 28. After the device is sufficiently expanded with fill material 30, two elastic cuffs 32A, 32B can be positioned over the outside diameter (OD) of the cannula 26 and pushed down the cannula 26, using a pusher 34 or any other suitable device, and onto the OD of the balloon 28, such that the cuffs 32A, 32B sufficiently seal or secure the proximal end 27 of the device 28 (see FIGS. 11A-11B). After the cuffs 32A, 32B are in place, the proximal end 27 of the device 28 can be severed, and the sheath 24 and cannula 26 can be removed from the GSV 10, leaving the inflated balloon 28 in an occlusive position within the GSV 10.

Turning now to a discussion of securing an occlusion device 28 within the GSV 10, in still alternative embodiments, the occlusion device 28 can be anchored if necessary. In an illustrative embodiment, for example, the proximal end 27 of the device can be secured to a suitable portion of the patient to assist in anchoring the device 28 in the GSV 10. Suitable anchoring locations include the GSV 10, a portion of the leg surrounding the access site, or a portion of a muscular or dermal layer within the leg. Any suitable securing means can be used to anchor the proximal end 27 of the balloon, such as any combination of sutures, clamps, clips, staples, energy-based fusion, ties, or the tying of at least a portion of the balloon to and/or around a secure structure, or the like. Further, any number of anchoring devices, such as barbs, clips, sutures, or the like can be placed along one or multiple locations of the device's 28 wall or body to assist in securing the balloon 28 within the GSV.

Figure 13:
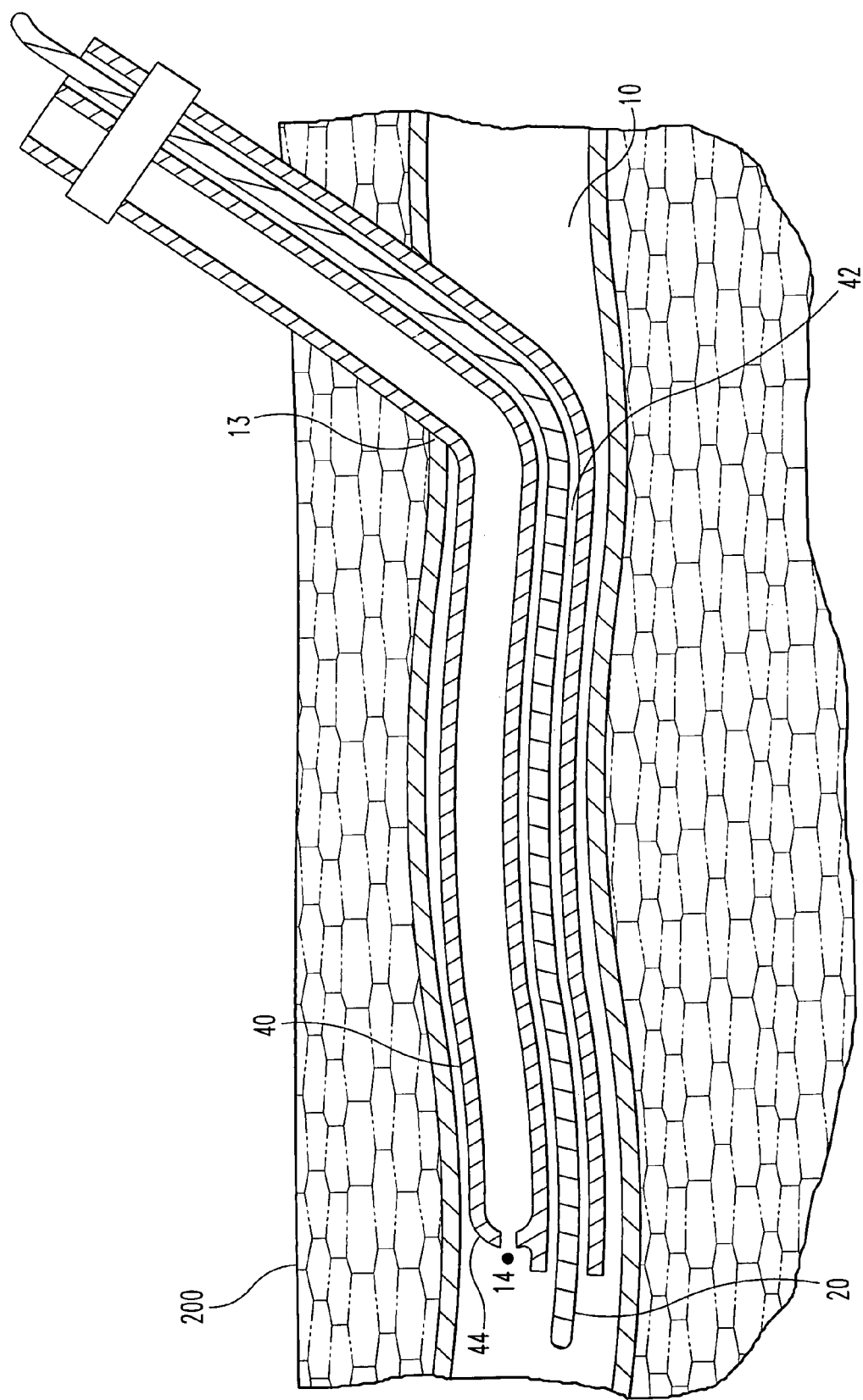
FIG. 13 depicts an illustrative deployment embodiment of the invention in that portion of the human leg occurring generally between points 13 and 14 in FIG. 1.
Figure 14:
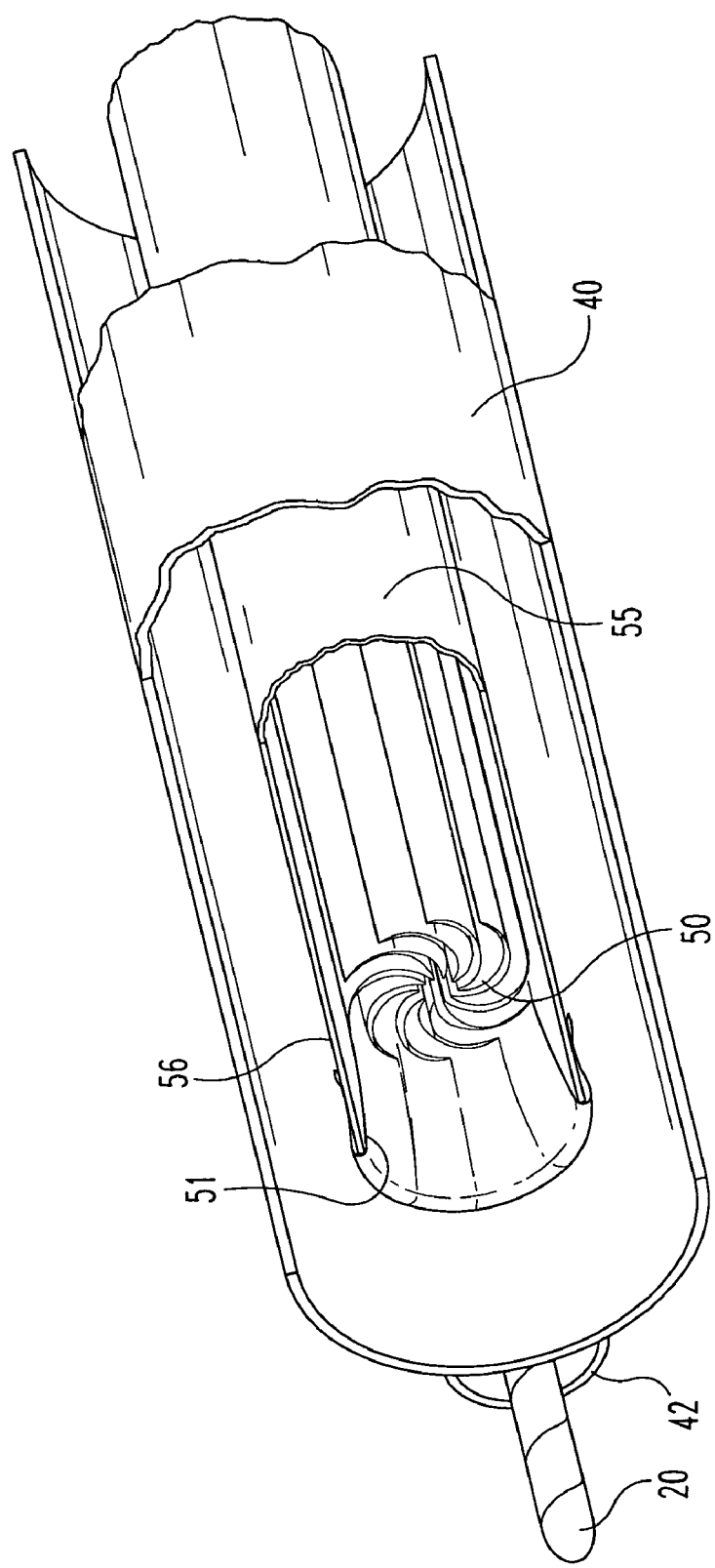
FIG. 14 depicts an illustrative balloon-loading and deployment embodiment of the present invention.

Turning now to a discussion of alternative deployment methods involving the use of a sheath with an external wire port, reference can be made to FIGS. 12 through 14. In an illustrative embodiment as shown in FIG. 12, a sheath 40 having an external wire port 42 can be located in the GSV 10 between points 13 and 14. In locating the sheath 40, percutaneous access to the GSV 10 can be achieved at point 13 and a wire guide 20 can be placed within the GSV 10 as shown in FIG. 12. After the wire guide 20 is placed, the sheath 40 with external wire guide port 42 can be received over the wire guide 20 and pushed to any suitable location within the GSV 10.

In an alternative embodiment, as shown in FIG. 13, the sheath 40 with external wire guide port 42 can have a compliant tip 44 that provides for easy tracking of the sheath through a patient's skin, tissue, and vasculature, while also readily opening to provide egress to an object traveling through the sheath's 40 lumen. Alternatively, in illustrative embodiments, the distal end of the sheath can be configured in any suitable shape or form, or include any suitable tip, to promote the ability of the sheath's distal end to be atraumatic while traveling in a bodily lumen. In an embodiment, for example, the sheath's distal end can include an angle, such as a 45 degree angle, that transverses the sheath's distal end.

Additionally, while the wire guide port 42 is depicted in FIGS. 12 and 13 as extending along the entire length of the deployment sheath 40, in alternative embodiments, for example, the wire guide port 42 can extend in intermittent aligned segments along the sheath 40, or still alternatively, can comprise a short tubular segment located at the sheath's 40 distal end.

Turning now to FIG. 14, shown is an embodiment for deploying an inverted occlusion device 50 through a sheath 40 having an unobstructed lumen and an external wire guide port 42. In this embodiment, the inflatable occlusion device 50 can be folded in a controlled fashion in order to improve its packing density within the cannula 55. This increased packing density can result in advantageously smaller delivery system components by reducing the required diameter of the cannula 55 and sheath 40.

Turning now to a discussion of balloon folding techniques, reference can be made again to FIG. 14. In illustrative embodiments, a flaccid balloon, such as one having walls constructed of a flaccid ECM or other collagenous or resorbable material, can be folded into any suitable shape using any suitable method, so as to reduce the cross-sectional diameter of the balloon. In an illustrative embodiment, shown in FIG. 14, the body of the balloon 50 can be folded or packed into a circular saw tooth pattern, using, for example, a balloon packing machine that evacuates the interior of the balloon while imparting a controlled fold to the body of the balloon. These and other similar patterns may include a plurality of folded portions that generally form arcuate segments that at least partially overlay adjacent arcuate segments, preferably forming overall a cylindrical, folded body. In the embodiment depicted in FIG. 14, the proximal end of the balloon 51 is not folded during the above folding process, so that it can be secured to the distal end 56 of the cannula 55 using any suitable means as discussed above. In illustrative embodiments, the proximal end 51 of the occlusion device 50 is secured to the distal end 56 of the cannula 55 after the balloon 50 is folded and placed within the lumen of the cannula 55.

Figure 15:
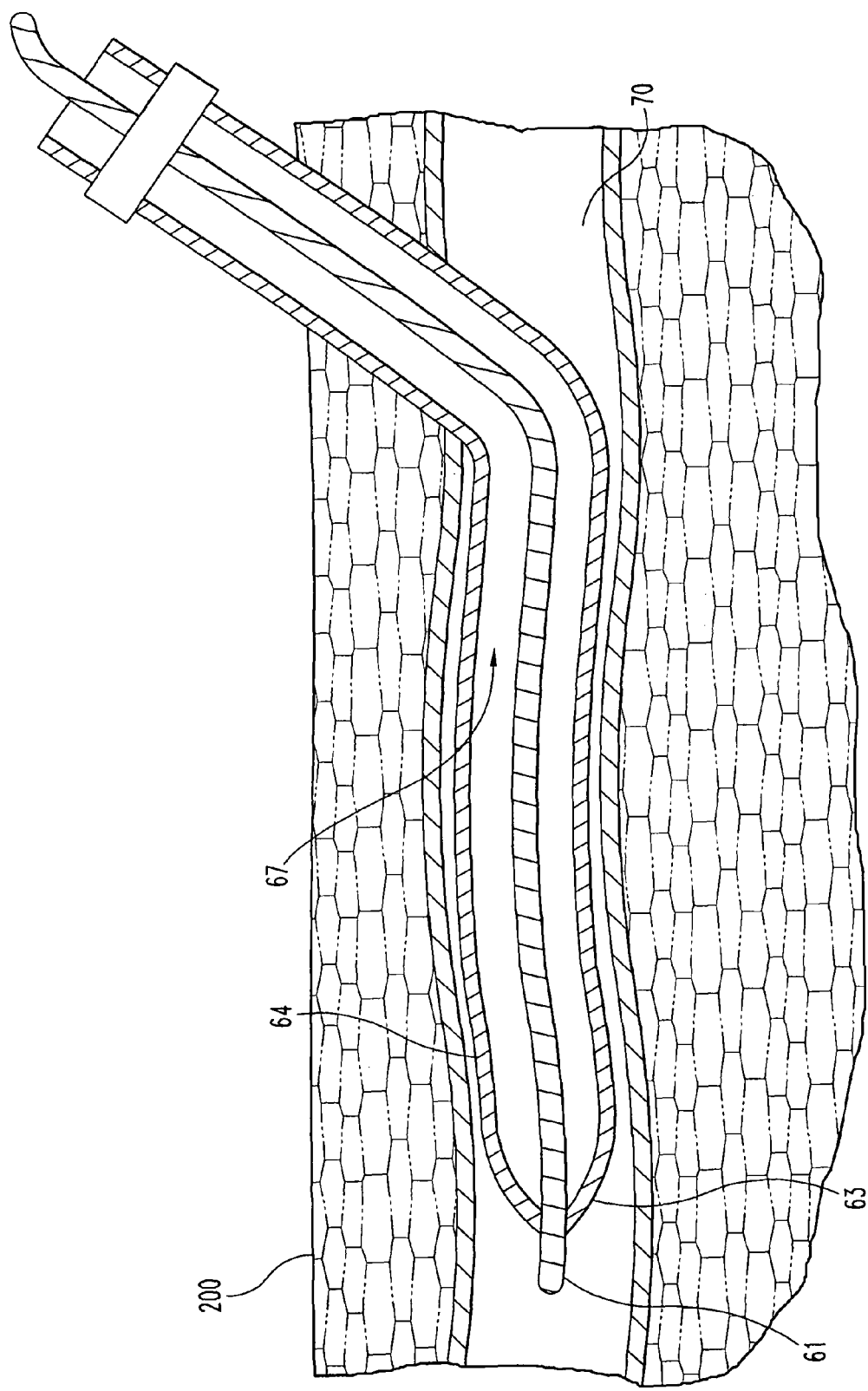
FIG. 15 depicts an illustrative deployment embodiment of the invention in that portion of the human leg occurring generally between points 13 and 14 in FIG. 1.
Figure 16:
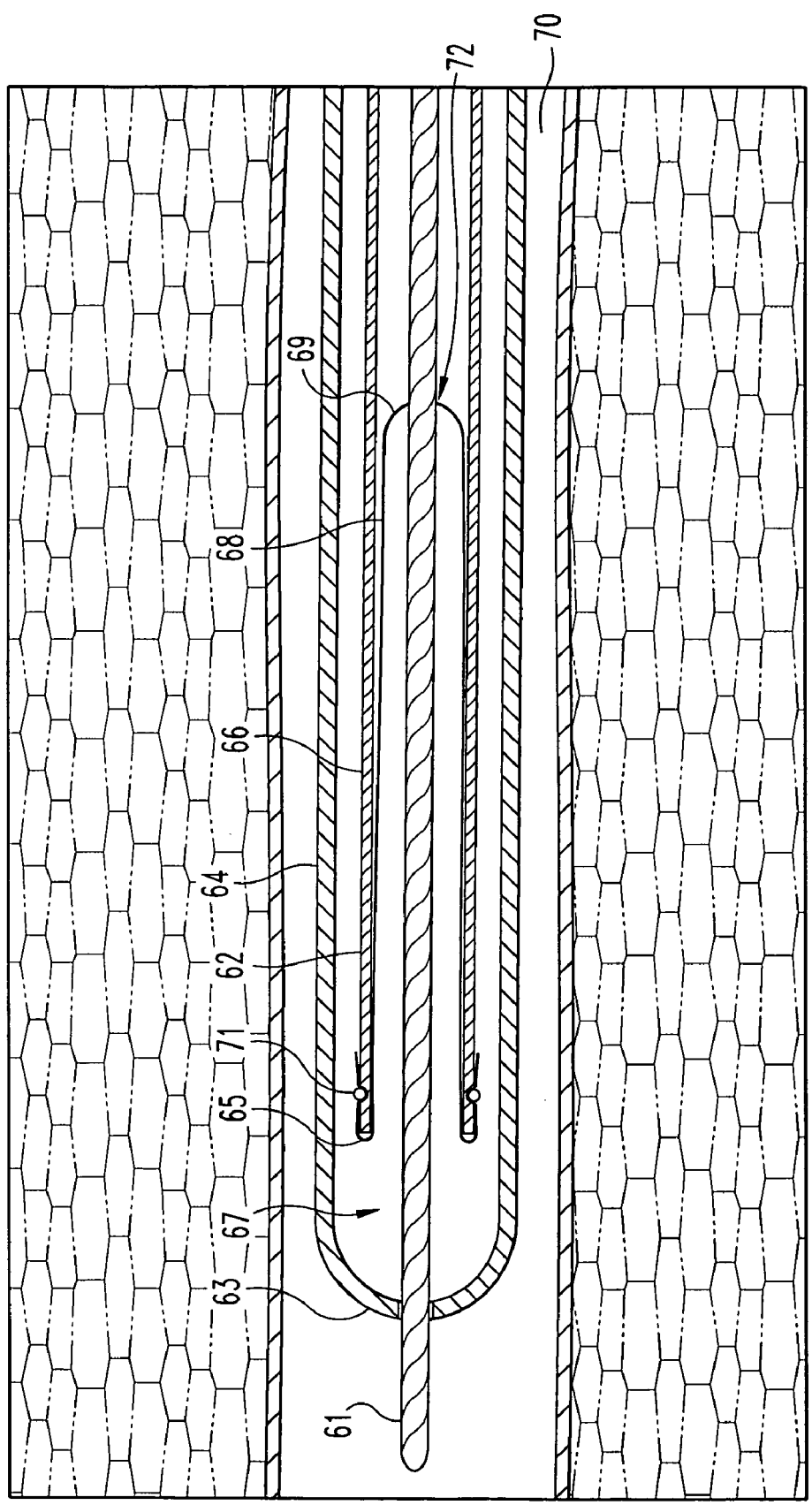
FIG. 16 depicts an illustrative balloon-loading and deployment embodiment of the present invention.
Figure 17:
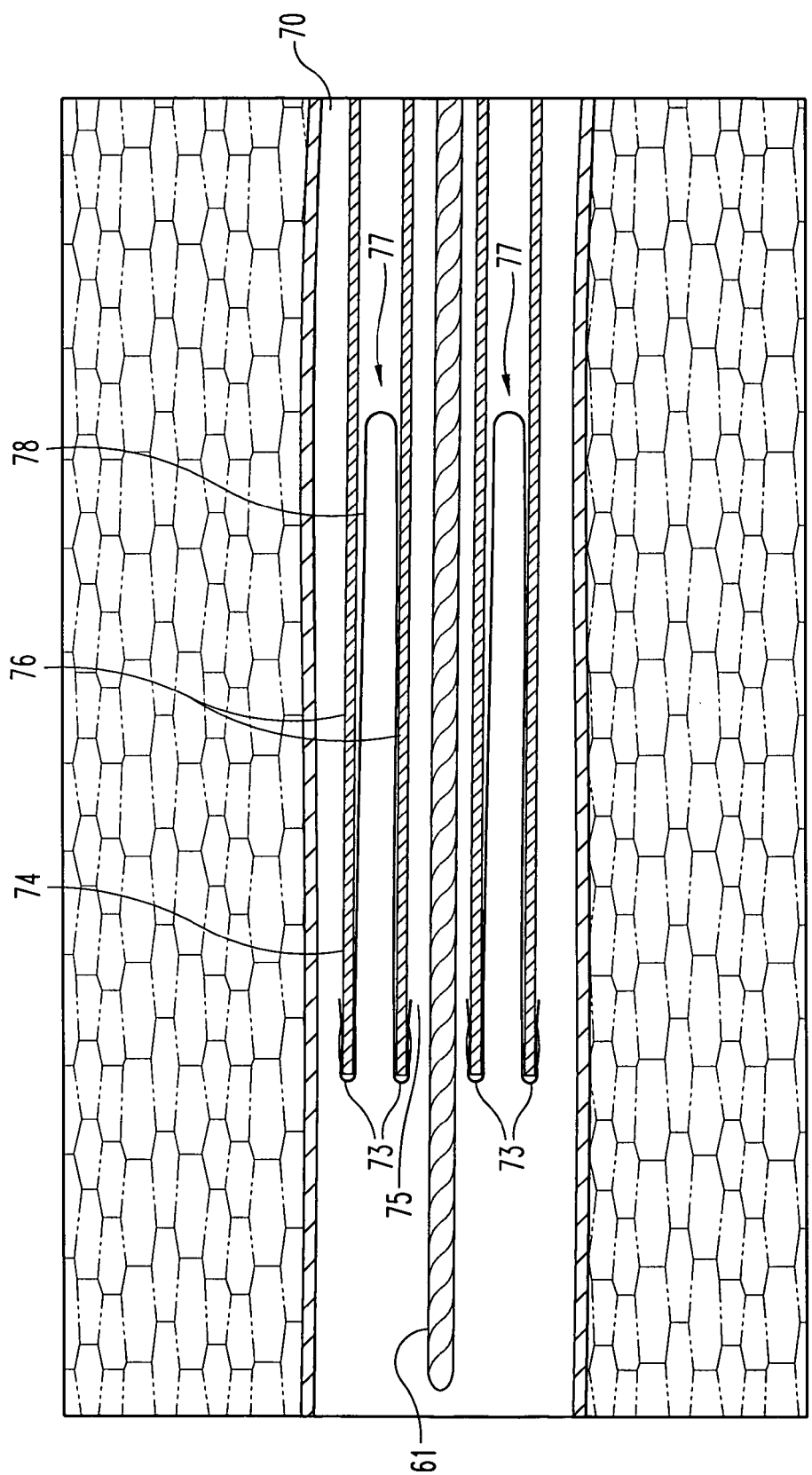
FIG. 17 depicts an illustrative balloon-loading and deployment embodiment of the present invention.

Turning now to a discussion of other alternative deployment methods of the invention, reference can be made to FIGS. 15 through 17, which demonstrate various over-the-wire deployment embodiments. With reference to FIG. 15, an illustrative embodiment is shown where the distal end of a deployment sheath 64 having a compliant tip 63 is located within a vascular vessel 70 by tracking the sheath 64 over a previously located wire guide 61. Once the sheath 64 is located within the vascular vessel 70, a number of alternative over the wire balloon deployment methods can be used to deploy an inflatable occlusion device in the vessel 70 while leaving the wire guide 61 disposed within the lumen 67 of the sheath 64.

For example, turning to FIG. 16, an embodiment is shown where an inverted occlusion device 68 is delivered to a location within a vascular vessel 70 over a wire guide 61 that is received within the lumen 67 of a deployment sheath 64 that has a compliant tip 63. In FIG. 16, the proximal end 65 of the occlusion device 68 is attached to the distal end 62 of the delivery cannula 66 by use of a compression ring 71 which snaps into a groove located in the cannula's 66 distal end 62. Further, the distal end 69 of the inverted balloon 68 contains a hole 72 for slidably receiving the wire guide 61. In this embodiment, the cannula 66 and the inverted balloon 68 are threaded onto the wire guide 61 and then pushed to the end of the deployment sheath 64. Once at the end of the sheath 64, the cannula 66 is held stationary, while the sheath 64 is retracted proximally. The retraction of the sheath 64 forces the compliant tip 63 to open, thereby delivering the distal end 62 of the cannula 66 into the vessel 70, where the balloon 68 can be deployed using any suitable method discussed above.

Once the wire guide 61 is retracted, the distal end 69 of the balloon can be closed using any suitable closing device or technique, such as any suitable combination of sutures, staples, clamps, clips, elastic cuffs, fusion bonding, or by tying the proximal end of the device into one or more knots. Alternatively, fill material having a diameter larger than the hole 72 can be used to inflate the balloon, thereby sealing the hole 72 upon inflation. Still alternatively, the proximal end can be closed, for example, by incorporating any suitable device or means for both closing and receiving a wire guide into the distal end 69 of the occluder, such as a flapper valve or a duck bill valve. For more information on valves suitable for use in the present invention, reference can be made, for example, to U.S. Pat. Nos. 5,222,970, 5,779,672, 6,312,405, and/or 6,736,793.

In an alternative embodiment, for example, the cannula 66 and inverted occlusion device 68 of FIG. 16 can be pushed to a location within the vessel 70 over wire guide 61 in the absence of deployment sheath 64, if desirable, or alternatively, an introducer sheath can be used to provide access to the vessel lumen. Once sufficiently located in the vessel 70, the device 68 can be deployed using any suitable technique discussed above.

Turning now to FIG. 17, an embodiment is illustrated that shows an over-the-wire deployment method for an inverted double walled occlusion device 78. As depicted in FIG. 17, a suitable wire guide 61 can be located in a vascular vessel 70, using any suitable technique as discussed above, e.g. the Seldinger technique. After the wire guide 61 is located in the vessel 70, a double walled occlusion device 78 that is inverted within a double walled cannulated device 76 can be tracked over the wire guide 61 to a suitable location within the vessel 70 where the device 78 can then be deployed and expanded to occlude the vessel 70.

In an illustrative embodiment, depicted in FIG. 17, the proximal end 73 of the double walled occlusion device 78 can be affixed to the distal end 74 of the double walled cannulated device 76 using any suitable technique as discussed above. As shown, the walls of the cannulated device 76 form an internal lumen 75 for receiving a wire guide 61 and an annular lumen 77 for receiving the inverted balloon 78, as well as receiving a suitable means for deploying and/or expanding the balloon 78 from the annular lumen 77. In an illustrative embodiment, the cannulated device 76 can contain columns that periodically extend through the annular region 77 connecting the two lumens in order to provide support, as needed, to the internal lumen 75. Additionally, in an illustrative embodiment, the annular region 77 can be used to transfer fill material from a source, such as a syringe, into the occlusion device 78 in order to expand the occlusion device 78 to prevent fluid reflux through the vessel 70.

Alternatively, in another embodiment, for example, the double walled cannula 76 and balloon 78 of FIG. 17 can be delivered through the unobstructed lumen of a deployment sheath using any suitable techniques disclosed above. Additionally, a double walled cannulated device, e.g. a segmented double walled cannulated device, or multiple single walled cannulated devices, can be used to deploy multiple single walled balloons into a bodily lumen, as is necessary. For example, in certain illustrative embodiments, multiple balloons can be deployed simultaneously into one cross-sectional space of a bodily lumen, or, alternatively, can be deployed in succession in the same bodily lumen, or, still alternatively, in different interconnected bodily lumens, as is necessary, without removing the cannulated device from the patient's body.

Turning now to a discussion of certain embodiments of inverted occlusion devices of the invention and additional deployment embodiments thereof, reference can be made to illustrative embodiments displayed in FIGS. 18A through 20.

Figure 18A:
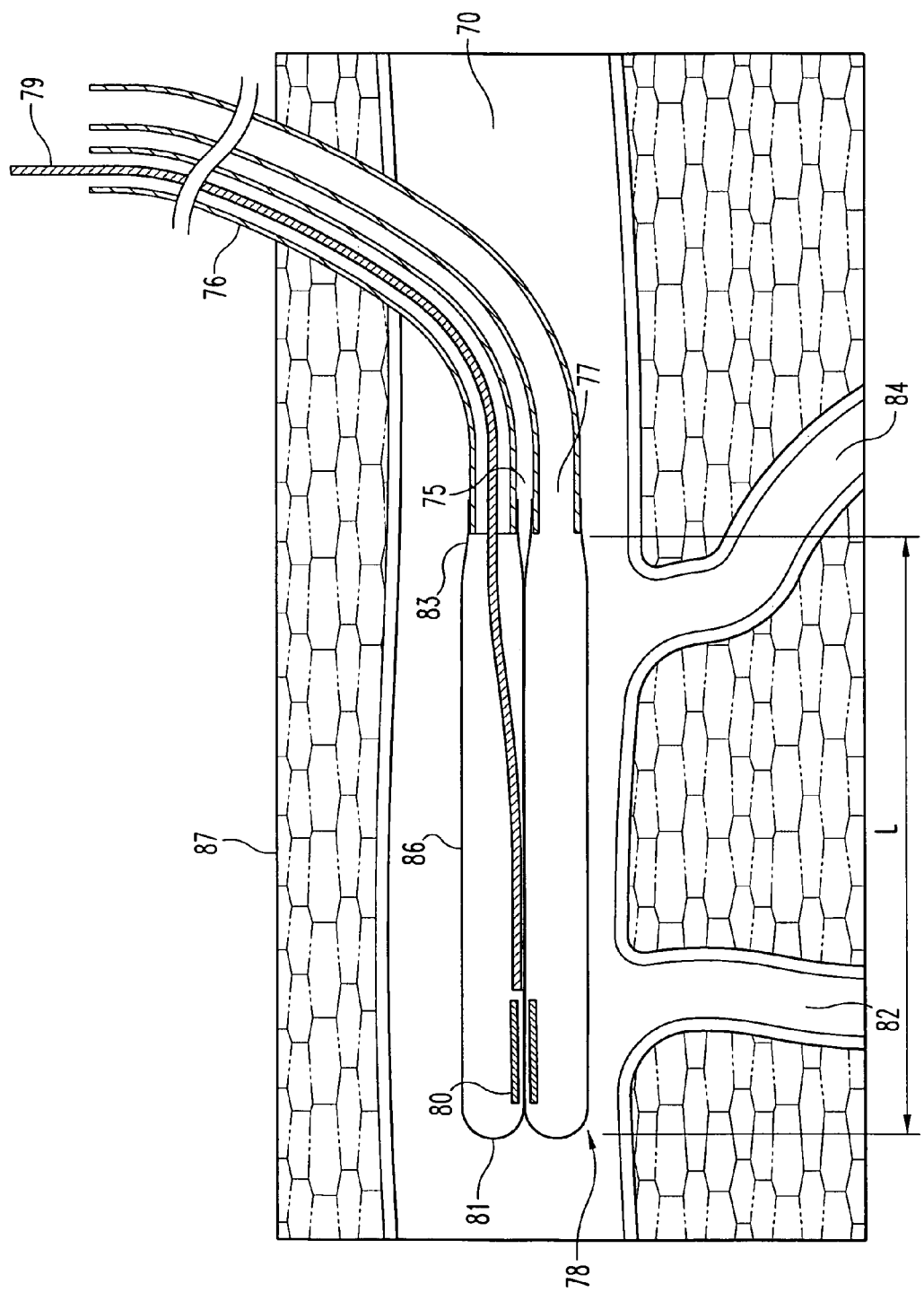
FIG. 18A depicts an illustrative balloon deployment embodiment of the present invention.
Figure 18B:
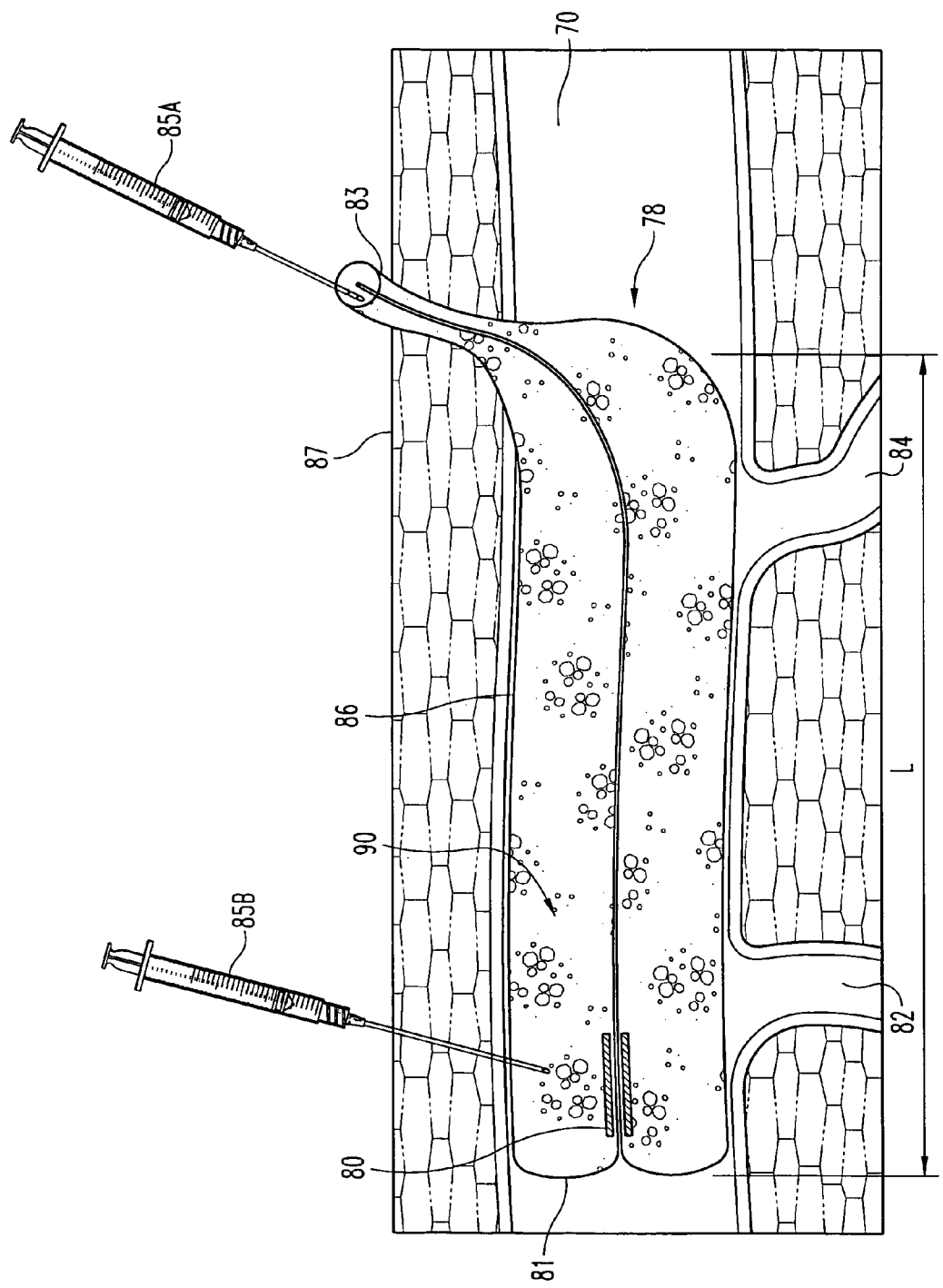
FIG. 18B depicts an illustrative balloon deployment embodiment of the present invention.

With reference now to FIGS. 18A and 18B, a cross-section taken along the vertical centerline of a partially deployed expandable occlusion device 78 is shown. The expandable occlusion device 78 in FIGS. 18A and 18B is a double walled balloon having an OD, an ID, a proximal end 83, a distal end 81, and a body 86. Device 78 has a length "L" sufficient to occlude the length of the passage for which occlusion or ablation is desired. In accordance with certain embodiments of the invention, the device 78 will have a length sufficient and will be positioned so as to traverse at least one vessel 82, 84 that branches from the vessel to be occluded 70, for instance a perforator or communicator vein branching from a larger vein to be occluded such as a saphenous vein, e.g. the GSV. In the context of GSV occlusion procedures as described above, length "L" will be sufficient to traverse the greater saphenous vein from position 13 to position 14, desirably having sufficient excess length to exit the percutaneous access site for filling, closure, and/or anchoring procedures. These same considerations may be applied to the other invertable inflatable vascular occlusion devices described herein.

With reference more specifically to FIG. 18A, a double walled balloon 78 is shown with a thin walled cannula 80 disposed over the balloon ID, yet within the balloon OD, and located at the balloon's 78 distal end 81. The cannula 80 can be positioned at the balloon's 78 distal end 81 by tracking it over the inner lumen 75 of the cannulated device 76 using a pusher 79, or any other suitable device and/or means. The location of the cannula 80 at the balloon's distal end 81 serves to promote closure of the balloon ID during expansion of the balloon with a suitable fill material.

Turning now to FIG. 18B, a continuation of the illustrative embodiment depicted in FIG. 18A, shown is the balloon 78 with its distal end 81 located at a suitable occlusion location within the vessel 70 and its proximal end 83 located outside the patient's body 87. The balloon's proximal end 83 can be located exterior to the patient's body 87 by retracting the cannulated device 76 from the vessel 70 and thereafter disconnecting the proximal end 83 of the balloon from the cannulated device 76 using any suitable means, such as a pair of surgical grade scissors. Next, the balloon 78 can be expanded using a suitable fill material 90. The fill material 90 can be transferred into the balloon using any suitable means, such as one or more syringe and needle pairs 85A, 85B. As shown in FIG. 18B, fill material 90 can be added to the balloon 78 at two different locations, at the same time, if desired. For example, the balloon 78 can be filled with one syringe and needle 85A at its proximal end 83 while simultaneously being filled toward its distal end 81 using a separate syringe and needle 85B that gains access to the balloon 78 through the patient's skin.

Figure 19A:
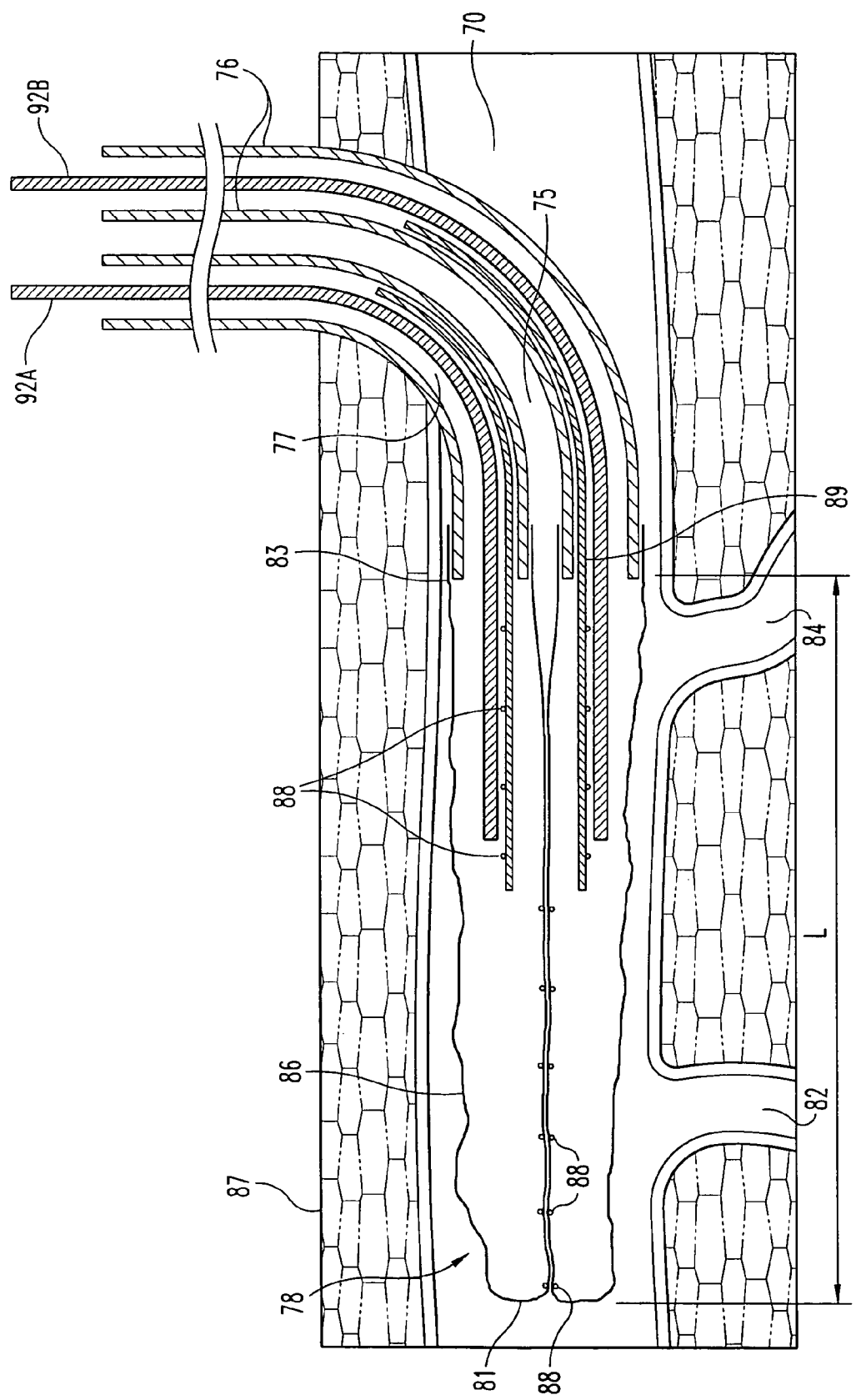
FIG. 19A depicts an illustrative balloon deployment embodiment of the present invention.

Turning now to FIG. 19A, an illustrative cross-section is shown of a partially deployed occlusion device 78 in a vascular vessel 70 of interest. The inflatable occlusion device 78 in FIG. 19A is a double walled balloon having an OD and an ID. The balloon 78 is shown in a partially deployed state with several elastic cuffs 88 positioned over the balloon's ID to ensure closure of the ID after deployment. The elastic cuffs 88 can be placed along the balloon 78 ID by tracking a thin walled cannula 89 loaded with multiple elastic cuffs 88 over the internal lumen 75 of the cannulated device 76 using one or more pushing devices if necessary 92A, 92B. In an illustrative embodiment, the thin walled cannula 89 can be used to deploy the balloon 78 from the annular lumen 77 of the cannulated device 76 by pushing the cannula 89 to the distal end 81 of the balloon 78. Once the balloon 78 is deployed, pushers 92A, 92B can be used to push the elastic cuffs 88 from the cannula 89 and onto the balloon 78 ID as the cannula is retracted in a proximal direction. If necessary, a suitable device, such as a gripper or the like, can be used to aid in the retraction of the thin walled cannula 89.

Figure 19B:
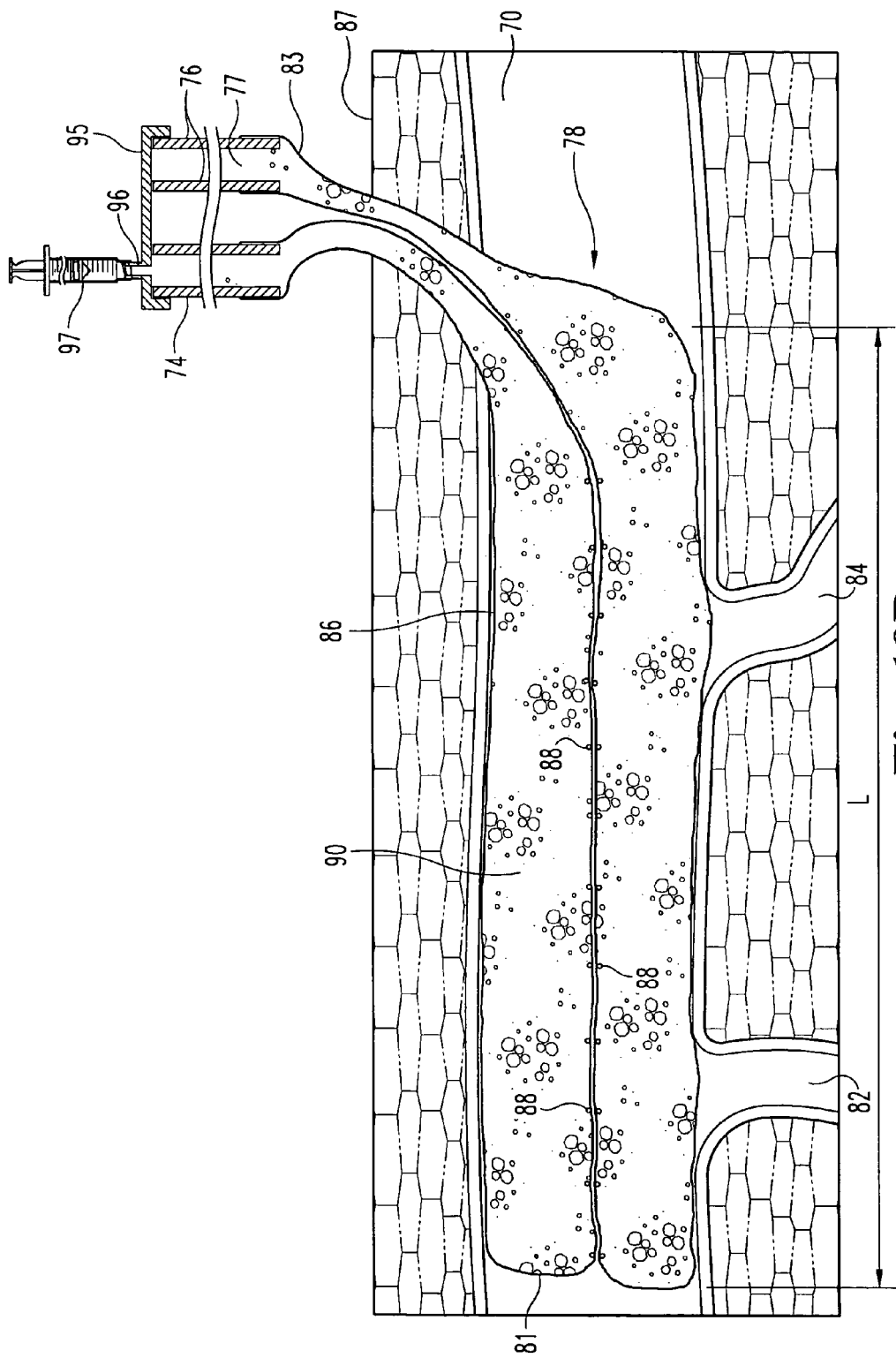
FIG. 19B depicts an illustrative balloon deployment embodiment of the present invention.

Turning now to FIG. 19B, which is an illustrative continuation of FIG. 19A, after the cuffs 88 are placed at suitable locations along the ID of the balloon, the cannulated device 76 can be removed from the vessel 70 such that the proximal end 83 of the balloon is located outside the patient's body 87. Next, a fill cap can be secured to the distal end 74 of the cannulated device 76 using any suitable means, such as a compression fitting, a threaded fitting, or clamps, or the like. As depicted in FIG. 19B, the fill cap seals at least the annular lumen 77 of the cannulated device 76 with the exception of at least one port 96 that provides a means for transferring fill material 90 from a device, such as a syringe and needle 97 into the balloon 78. After the fill cap 95 is secured to the cannulated device 76, the balloon 78 can be filled until it sufficiently occludes the vascular vessel of interest.

In an alternative deployment embodiment for a double walled balloon, the balloon can have an ID that is capable of closing by itself, so as to prevent blood reflux through the ID of the balloon. The self-closing functionality can be achieved in a number of ways, such as by constructing the balloon such that its ID closes upon inflation of the balloon with fill material. Alternatively, the ID of the balloon, or the entire balloon can be constructed with an elastic-type material, such that the balloon ID closes before, after, or during balloon deployment.

Although certain procedures have been described above for the delivery of occlusion devices, it will be understood that other modes of delivery of occlusion devices are also contemplated in embodiments of the present invention. For example, occlusive devices can be delivered within the vasculature using an introducer cannula so as to provide access to the vasculature with the cannula and deploy the device into an otherwise unoccupied or open vascular lumen. In such illustrative procedures, the distal end of the balloon can be inverted, such as within the lumen of the cannula, and reside at a proximal location, e.g. external to the cannula's proximal end until deployment of the device and/or occlusion of the vascular segment is achieved. In certain embodiments, each end of the inverted device can remain external to the vasculature during an illustrative deployment/occlusion procedure. In the context of occluding the greater saphenous vein, such techniques can be conducted with the percutaneous access site provided either at the knee level or near the groin in the area of the sapheno-femoral junction, or any appropriate location in between or otherwise. Further, it is contemplated within certain embodiments of the invention that cut-down or other surgical procedures could be used in providing access to vascular vessels for delivery of vascular occlusion devices.

Turning now to a discussion of alternative balloon filling methods, in an embodiment, a balloon can be filled on more than one occasion to combat the occurrence of patency in the occluded vessel. For example, in an illustrative embodiment, the balloon can be filled with fill material during placement of the balloon in the GSV. Then, during follow up patient visits, more fill material can be added to the balloon, if needed, using a suitable filling method, such as injecting the balloon with fill material using a syringe and needle.

In an alternative embodiment, additional fill material can be stored in a reservoir in communication with the balloon. The fill material can then be transferred from the reservoir to the balloon, as needed, using any suitable transfer method, such as a pressure differential. The reservoir can be located in any suitable location, extracutaneous or intracutaneous, as desired. In an embodiment, for example, the reservoir can be a silicone bulb secured in an extracutaneous location that is capable of receiving additional fill material via a syringe or, alternatively, a fill port.

In still other embodiments, differing material can be used to fill the balloon during and/or after deployment. For example, a first fill material, such as an aqueous medium, optionally containing an x-ray or other suitable contrast agent to visualize and confirm balloon position, can be used to deploy the balloon from its partially or completely inverted position, and a second, differing fill material can thereafter be delivered into the balloon. The first fill material can be withdrawn from the balloon through the delivery lumen, partially or completely, or may be supplemented or displaced by the delivery of the second material. For instance, the first fill material may be capable of passing through pores or openings in the balloon wall; whereas the second fill material is not or is more resistant to such passage.

Turning now to a discussion of suitable balloon or fillable member materials, the material used in the formation of illustrative occlusion devices of the invention can be any material suitable for occluding a vessel of interest. In this regard, the occlusion material may be a synthetic material such as a polymeric material, or a naturally-derived material, such as an extracellular matrix (ECM) material, e.g. in an elongate pouch form. Illustrative synthetic materials may include biodegradable or non-biodegradable materials. These include, for example, synthetic biocompatible polymers such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof; polylactic acid, polyglycolic acid or copolymers thereof; a polyanhydride, polycaprolactone, polyhydroxy-butyrate valerate, polyhydroxyalkanoate, or another biodegradable polymer.

Reconstituted or naturally-derived collagenous materials can also be used as occlusion materials in the present invention. Such materials that are at least bioresorbable will provide advantage in the present invention, with materials that are bioremodelable and promote cellular invasion and ingrowth providing particular advantage. Bioremodelable materials may be used in this context to promote cellular growth within the lumen of the occluded vessel. This helps to guard against re-establishment of patency of the vessel through biologic processes after the occlusion procedure is completed.

Collagenous ECM materials can be used in the formation of illustrative occlusion devices of the invention, including bioremodelable ECM materials. These can be delivered to the vessel in a lyophilized or otherwise dried or hydrated state. For example, suitable collagenous materials include ECM material such as submucosa, renal capsule membrane, dermal collagen, dura mater, pericardium, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. The preferred occlusion devices of the invention will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa, more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Additionally, suitable fillable members or balloon materials can be obtained by isolating tubular or elongate pouch form ECM materials, such as, for example, small stomachs, urinary bladders, vascular vessels, ureters, and/or suitable portions of the gastrointestinal (GI) tract. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

As prepared and used, the submucosa material and any other ECM material used, may optionally retain growth factors or other bioactive components native to the source tissue. For example, the submucosa or other ECM material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in embodiments of the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Further, in addition or as an alternative to the inclusion of such native bioactive components, non-native bioactive components such as those synthetically produced by recombinant technology or other methods, may be incorporated into the submucosa tissue. These non-native bioactive components may be naturally-derived or recombinantly produced proteins that correspond to those natively occurring in the ECM material tissue, but perhaps of a different species (e.g. human proteins applied to collagenous ECMs from other animals, such as pigs). The non-native bioactive components may also be drug substances. Illustrative drug substances that may be incorporated into and/or onto the occlusion devices include, for example, antibiotics, thrombus-promoting substances such as blood clotting factors, e.g. thrombin, fibrinogen, and the like. These substances may be applied to the occlusion device as a premanufactured step, immediately prior to the procedure (e.g. by soaking the material in a solution containing a suitable antibiotic such as cefazolin), or during or after deployment of the occlusion device in the patient.

Submucosa or other ECM tissue used in embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in the invention is preferably disinfected with an oxidizing agent, particularly a peracid, such as peracetic acid. These and additional properties of submucosa or other ECM tissue taught in U.S. Pat. No. 6,206,931 may be characteristic of the submucosa tissue used in the present invention.

Alternatively or additionally, other suitable occlusion balloon materials include, substantially non-antigenic elastic materials, latex, and silicone. For more information on suitable balloon materials that can be used in the present invention, reference can be made, for example, to U.S. Pat. Nos. 4,819,637, 5,222,970, 5,304,123, 5,411,475, 5,779,672, and/or 5,830,228.

The remodelable ECM or other material may include one or more radiopaque and/or ecogenic markers or a radiopaque coating or impregnation to assist in visualization of the material during a non-invasive procedure. For example, radiopaque substances containing tantalum, barium, iodine, or bismuth, e.g. in powder form, can be coated upon or incorporated within the ECM or other remodelable material, such that, for example, the location of the balloon's distal end is detectable.

Turning now to a discussion of inventive fill materials, the occlusion device can be filled with any material conducive to achieving occlusion of a vascular or other vessel of interest. In this regard, the fill material may be a solid, liquid, gel, foam, or gas, such as a collagenous fill material, blood, polymer, contrast medium, a remodelable or bioabsorbable material, saline, a non-bioabsorbable material, collagen rods or particulates, a collagenous or gelatinous foam, air, chitosan, gelatin, oxidized regenerated cellulose, calcium alginate, alginate, thrombin-fibrin enhanced materials, fibrin glues, or any suitable combination thereof.

In an illustrative embodiment, the fill material can comprise a comminuted, fluidized, and/or gelatinous remodelable material. For example, a remodelable gel can be formed from fluidized compositions, as illustrated in U.S. Pat. Nos. 5,275,826, 5,516,533, 6,206,931, and/or 6,444,229. Fluidized or otherwise flowable ECM compositions may also be prepared as described in co-pending International Patent Application No. WO2005/020847 (PCT/US04/27557) filed Aug. 25, 2004 and entitled Graft Materials Containing Bioactive Substances, and Methods for Their Manufacture. In this regard, the flowable fill compositions used in the invention can be prepared from an isolated ECM material, for example one of those listed above. The ECM material can be used to prepare a solubilized mixture including components of the material. This can be achieved by digestion of the ECM material in an acidic or basic medium and/or by contact with an appropriate enzyme or combination of enzymes.

For example, in an illustrative preparative embodiment, fill material can be made by first reducing ECM material to particulate form to aid in a digestion step. This can be achieved by tearing, cutting, grinding or shearing the isolated ECM material. Illustratively, shearing may be conducted in a fluid medium, and grinding may be conducted with the material in a frozen state. For example, the material can be contacted with liquid nitrogen to freeze it for purposes of facilitating grinding into powder form. Such techniques can involve freezing and pulverizing submucosa under liquid nitrogen in an industrial blender.

Next, the reduced ECM material can be subjected to digestion using any suitable enzyme in an enzymatic digestion step. Such enzymes include for example serine proteases, aspartyl proteases, and matrix metalloproteases. The concentration of the enzyme can be adjusted based on the specific enzyme used, the amount of submucosa to be digested, the duration of the digestion, the temperature of the reaction, and the desired properties of the remodelable fill material. In an illustrative embodiment, about 0.1% to about 0.2% of enzyme (pepsin, for example) can be used and the digestion can be conducted under cooled conditions for a period of time sufficient to substantially digest the ECM material. The digestion can be conducted at any suitable temperature, with temperatures ranging from 4° to 37° C. being preferred. Likewise, any suitable duration of digestion can be used, such durations typically falling in the range of about 2 to 180 hours. The ratio of the concentration of ECM material (hydrated) to total enzyme usually ranges from about 25 to about 125 and more typically the ratio is about 50, and the digestion is conducted at approximately 4° C. for approximately 24-72 hours. When an enzyme is used to aid in the digestion, the digestion will be performed at a pH at which the enzyme is active and more advantageously at a pH at which the enzyme is optimally active. Illustratively, pepsin exhibits optimal activity at pH's in the range of about 2 to 4.

The enzymes or other disruptive agents used to solubilize the ECM material during formation of a suitable fill material can be removed or inactivated before or during the gelling process so as not to compromise gel formation or subsequent gel stability. Also, any disruptive agent, particularly enzymes, that remains present and active during storage of the tissue can potentially change the composition and potentially the gelling characteristics of the solution. Enzymes, such as pepsin, can be inactivated with protease inhibitors, a shift to neutral pH, a drop in temperature below 0° C., heat inactivation, or through the removal of the enzyme by fractionation. A combination of these methods can be utilized to stop digestion of the ECM material at a predetermined endpoint, for example the ECM material can be immediately frozen and later fractionated to limit digestion.

Illustratively, during preparation of a suitable fill material, the ECM material can be enzymatically digested for a sufficient time to produce a hydrolysate of ECM components. Accordingly, the ECM can be treated with one enzyme or with a mixture of enzymes to hydrolyze the structural components of the material and prepare a hydrolysate having multiple hydrolyzed components of reduced molecular weight. The length of digestion time can be varied depending on the application, and the digestion can be extended to completely solubilize the ECM material. In some modes of operation, the ECM material will be treated sufficiently to partially solubilize the material to produce a digest composition comprising hydrolyzed ECM components and nonhydrolyzed ECM components. The digest composition can then, in illustrative embodiments, be further processed to remove at least some of the nonhydrolyzed components. For example, the nonhydrolyzed components can be separated from the hydrolyzed portions by centrifugation, filtration, or other separation techniques known in the art.

Illustratively, preferred gel form fill material compositions can be prepared from enzymatically digested vertebrate ECM material that has been fractionated under acidic conditions, for example including pH ranging from about 2 to less than 7, especially to remove low molecular weight components. Typically, the ECM hydrolysate is fractionated by dialysis against a solution or other aqueous medium having an acidic pH, e.g. a pH ranging from about 2 to about 5, more desirably greater than 3 and less than 7. In addition to fractionating the hydrolysate under acidic conditions, the ECM hydrolysate is typically fractionated under conditions of low ionic strength with minimal concentrations of salts such as those usually found in standard buffers such as PBS (i.e. NaCl, KCl, $Na_2HPO_4$, or $KH_2PO_4$) that can pass through the dialysis membrane and into the hydrolysate. Such fractionation conditions work to reduce the ionic strength of the ECM hydrolysate and thereby provide enhanced gel forming characteristics.

The hydrolysate solution produced by enzymatic digestion of the ECM material has a characteristic ratio of protein to carbohydrate. The ratio of protein to carbohydrate in the hydrolysate is determined by the enzyme utilized in the digestion step and by the duration of the digestion. The ratio may be similar to or may be substantially different from the protein to carbohydrate ratio of the undigested ECM tissue. For example, digestion of vertebrate ECM material with a protease such as pepsin, followed by dialysis, will form a fractionated ECM hydrolysate having a lower protein to carbohydrate ratio relative to the original ECM material.

Flowable ECM compositions capable of forming shape retaining gels can be used as fill material in the present invention. Illustrative such ECM compositions can be prepared from ECM material that has been enzymatically digested and fractionated under acidic conditions to form an ECM hydrolysate that has a protein to carbohydrate ratio different than that of the original ECM material. Such fractionation can be achieved entirely or at least in part by dialysis. The molecular weight cut off of the ECM components to be included in the gellable material is selected based on the desired properties of the gel. Typically the molecular weight cutoff of the dialysis membrane (the molecular weight above which the membrane will prevent passage of molecules) is within in the range of about 2000 to about 10000 Dalton, and more preferably from about 3500 to about 5000 Dalton.

In certain forms of the gellable ECM fill material composition, apart from the potential removal of undigested ECM components after the digestion step and any controlled fractionation to remove low molecular weight components as discussed above, the ECM hydrolysate is processed so as to avoid any substantial further physical separation of the ECM components. For example, when a more concentrated ECM hydrolysate material is desired, this can be accomplished by removing water from the system (e.g. by evaporation or lyophilization) as opposed to using conventional "salting out"/centrifugation techniques that would demonstrate significant selectivity in precipitating and isolating collagen, leaving behind amounts of other desired ECM components. Thus, in certain embodiments of the invention, solubilized ECM components of the ECM hydrolysate remain substantially unfractionated, or remain substantially unfractionated above a predetermined molecular weight cutoff such as that used in the dialysis membrane, e.g. above a given value in the range of about 2000 to 10000 Dalton, more preferably about 3500 to about 5000 Dalton.

In the manufacture of suitable fill material, vertebrate ECM material can be stored frozen (e.g. at about −20 to about −80° C.) in either its solid, comminuted or enzymatically digested forms, or the material can be stored after being hydrolyzed and fractionated. The ECM material can be stored in solvents that maintain the collagen in its native form and solubility. For example, one suitable storage solvent is 0.01 M acetic acid, however other acids can be substituted, such as 0.01 N HCl. In one form, the fractionated ECM hydrolysate can be dried (by lyophilization, for example) and stored in a dehydrated/lyophilized state. The dried form can be rehydrated to prepare a flowable ECM composition capable of forming a gel that can be used as a fill material in the present invention.

In accordance with an illustrative method of fill material preparation, the fractionated ECM hydrolysate or other flowable ECM composition will exhibit the capacity to gel upon adjusting the pH of a relatively more acidic aqueous medium containing it to about 5 to about 9, more preferably about 6.6 to about 8.0, and typically about 7.2 to about 7.8, thus inducing fibrillogenesis and matrix gel assembly. In one embodiment, the pH of the fractionated hydrolysate can be adjusted by the addition of a buffer that does not leave a toxic residue, and has a physiological ion concentration and the capacity to hold physiological pH. Examples of suitable buffers include PBS, HEPES, and DMEM. Illustratively, the pH of the fractionated ECM hydrolysate can be raised by the addition of a buffered NaOH solution to 6.6 to 8.0, more preferably 7.2 to 7.8, to facilitate the formation of an ECM-containing gel. Any suitable concentration of NaOH solution can be used for these purposes, for example including about 0.05 M to about 0.5 M NaOH. In accordance with an embodiment, the ECM hydrolysate is mixed with a buffer and sufficient 0.25 N NaOH is added to the mixture to achieve the desired pH.

The ionic strength of the ECM hydrolysate is believed to be important in maintaining the fibers of collagen in a state that allows for fibrillogenesis and matrix gel assembly upon neutralization of the hydrolysate. Accordingly, if needed, the salt concentration of the ECM hydrolysate material can be reduced prior to neutralization of the hydrolysate. The neutralized hydrolysate can be caused to gel at any suitable temperature, e.g. ranging from about 4° C. to about 40° C. The temperature will typically affect the gelling times, which may range from about 5 to about 120 minutes at the higher gellation temperatures and about 1 to about 8 hours at the lower gellation temperatures. Typically, the hydrolysate will be effective to self-gel at elevated temperatures, for example at about 37° C. In this regard, preferred neutralized ECM hydrolysates will be effective to gel in less than about ninety minutes at 37° C., for example approximately thirty to ninety minutes at 37° C.

In alternative embodiments, additional components can be added to the ECM hydrolysate composition before, during, or after forming the gelatinous fill material composition. For example, proteins carbohydrates, growth factors, as discussed above, therapeutics, bioactive agents, nucleic acids, cells or pharmaceuticals can be added. In certain embodiments, such materials are added prior to formation of the gel. This may be accomplished for example by forming a dry mixture of a powdered ECM hydrolysate with the additional component(s), and then reconstituting and gelling the mixture, or by incorporating the additional component(s) into an aqueous, ungelled composition of the ECM hydrolysate before, during (e.g. with) or after addition of the neutralization agent. The additional component(s) can also be added to the formed ECM gel, e.g. by infusing or mixing the component(s) into the gel and/or coating them onto the gel.

In an illustrative fill material preparation embodiment, a particulate ECM material can be added to an ECM hydrolysate composition, which can then be incorporated in the formed gel. Such particulate ECM materials can be prepared by cutting, tearing, grinding or otherwise comminuting an ECM starting material. For example, a particulate ECM material having an average particle size of about 50 microns to about 500 microns may be included in the gellable ECM hydrolysate, more preferably about 100 microns to about 400 microns. The ECM particulate can be added in any suitable amount relative to the hydrolysate, with preferred ECM particulate to ECM hydrolysate weight ratios (based on dry solids) being about 0.1:1 to about 200:1, more preferably in the range of about 1:1 to about 100:1. The inclusion of such ECM particulates in the ultimate gelatinous fill material can serve to provide additional material that can function to provide bioactivity to the gel (e.g. itself including FGF-2 and/or other growth factors or bioactive substances as discussed herein) and/or serve as scaffolding material for tissue ingrowth.

In certain embodiments, an ECM hydrolysate material to be used as a fill material in the invention will exhibit an injectable character and also incorporate an ECM particulate material. In these embodiments, the ECM particulate material can be included at a size and in an amount that effectively retains an injectable character to the hydrolysate composition.

In certain embodiments, flowable ECM compositions to be used as fill material in the invention may be disinfected by contacting an aqueous medium including ECM hydrolysate components with an oxidizing disinfectant. This mode of disinfection provides an improved ability to recover a disinfected ECM hydrolysate that exhibits the capacity to form beneficial gels. In certain preparative methods, an aqueous medium containing ECM hydrolysate components can be disinfected by providing a peroxy disinfectant in the aqueous medium. This can be advantageously achieved using dialysis to deliver the peroxy disinfectant into and/or to remove the peroxy disinfectant from the aqueous medium containing the hydrolysate. In certain dinsinfection techniques, an aqueous medium containing the ECM hydrolysate is dialyzed against an aqueous medium containing the peroxy disinfectant to deliver the disinfectant into contact with the ECM hydrolysate, and then is dialyzed against an appropriate aqueous medium (e.g. an acidic aqueous medium) to at least substantially remove the peroxy disinfectant from the ECM hydrolysate. During this dialysis step, the peroxy compound passes through the dialysis membrane and into the ECM hydrolysate, and contacts ECM components for a sufficient period of time to disinfect the ECM components of the hydrolysate. In this regard, typical contact times will range from about 0.5 hours to about 8 hours and more typically from about 1 hour to about 4 hours. The period of contact will be sufficient to substantially disinfect the digest, including the removal of endotoxins and inactivation of virus material present. The removal of the peroxy disinfectant by dialysis may likewise be conducted over any suitable period of time, for example having a duration of about 4 to about 180 hours, more typically of about 24 to about 96 hours. In general, the disinfection step will desirably result in a disinfected ECM hydrolysate composition having sufficiently low levels of endotoxins, viral burdens, and other contaminant materials to render it suitable for use as a fill material in an occlusion device. Endotoxin levels below about 2 endotoxin units (EUs) per gram (dry weight) are preferred, more preferably below about 1 EU per gram, as are virus levels below 100 plaque forming units per gram (dry weight), more preferably below 1 plaque forming unit per gram.

The aqueous ECM hydrolysate composition can be a substantially homogeneous solution during the dialysis step for delivering the oxidizing disinfectant to the hydrolysate composition and/or during the dialysis step for removing the oxidizing disinfectant from the hydrolysate composition. Alternatively, the aqueous hydrolysate composition can include suspended ECM hydrolysate particles, optionally in combination with some dissolved ECM hydrolysate components, during either or both of the oxidizing disinfectant delivery and removal steps. Dialysis processes in which at least some of the ECM hydrolysate components are dissolved during the disinfectant delivery and/or removal steps are preferred and those in which substantially all of the ECM hydrolysate components are dissolved are more preferred.

The disinfection step can be conducted at any suitable temperature, and will typically be conducted between about 0° C. and about 37° C., more typically between about 4° C. and about 15° C. During this step, the concentration of the ECM hydrolysate solids in the aqueous medium can be in the range of about 2 mg/ml to about 200 mg/ml, and may vary somewhat through the course of the dialysis due to the migration of water through the membrane. In certain embodiments, a relatively unconcentrated digest is used, having a starting ECM solids level of about 5 mg/ml to about 15 mg/ml. In other embodiments, a relatively concentrated ECM hydrolysate is used at the start of the disinfection step, for example having a concentration of at least about 20 mg/ml and up to about 200 mg/ml, more preferably at least about 100 mg/ml and up to about 200 mg/ml. It has been found that the use of concentrated ECM hydrolysates during this disinfection processing results in an ultimate gel composition having higher gel strength than that obtained using similar processing with a lower concentration ECM hydrolysate. Accordingly, processes which involve the removal of amounts of water from the ECM hydrolysate resulting from the digestion prior to the disinfection processing step are preferred. For example, such processes may include removing only a portion of the water (e.g. about 10% to about 98% by weight of the water present) prior to the dialysis/disinfection step, or may include rendering the digest to a solid by drying the material by lyophilization or otherwise, reconstituting the dried material in an aqueous medium, and then treating that aqueous medium with the dialysis/disinfection step.

In an illustrative fill material preparation embodiment, the disinfection of the aqueous medium containing the ECM hydrolysate can include adding the peroxy compound or other oxidizing disinfectant directly to the ECM hydrolysate, for example being included in an aqueous medium used to reconstitute a dried ECM hydrolysate or being added directly to an aqueous ECM hydrolysate composition. The disinfectant can then be allowed to contact the ECM hydrolysate for a sufficient period of time under suitable conditions (e.g. as described above) to disinfect the hydrolysate, and then removed from contact with the hydrolysate. In one embodiment, the oxidizing disinfectant can then be removed using a dialysis procedure as discussed above. In other embodiments, the disinfectant can be partially or completely removed using other techniques such as chromatographic or ion exchange techniques, or can be partially or completely decomposed to physiologically acceptable components. For example, when using an oxidizing disinfectant containing hydrogen peroxide (e.g. hydrogen peroxide alone or a peracid such as peracetic acid), hydrogen peroxide can be allowed or caused to decompose to water and oxygen, for example in some embodiments including the use of agents that promote the decomposition such as thermal energy or ionizing radiation, e.g. ultraviolet radiation.

In an alternative fill material preparation embodiment, the oxidizing disinfectant can be delivered into the aqueous medium containing the ECM hydrolysate by dialysis and processed sufficiently to disinfect the hydrolysate (e.g. as described above), and then removed using other techniques such as chromatographic or ion exchange techniques in whole or in part, or allowed or caused to decompose in whole or in part as discussed immediately above.

Peroxygen compounds that may be used in the disinfection step include, for example, hydrogen peroxide, organic peroxy compounds, and preferably peracids. Such disinfecting agents are used in a liquid medium, preferably a solution, having a pH of about 1.5 to about 10.0, more desirably of about 2.0 to about 6.0. As to peracid compounds that can be used, these include peracetic acid, perpropioic acid, and/or perbenzoic acid. Peracetic acid is the most preferred disinfecting agent for purposes of the present invention.

When used, peracetic acid is desirably diluted into about a 2% to about 50% by volume of alcohol solution, preferably ethanol. The concentration of the peracetic acid may range, for instance, from about 0.05% by volume to about 1.0% by volume. Most preferably, the concentration of the peracetic acid is from about 0.1% to about 0.3% by volume. When hydrogen peroxide is used, the concentration can range from about 0.05% to about 30% by volume. More desirably the hydrogen peroxide concentration is from about 1% to about 10% by volume, and most preferably from about 2% to about 5% by volume. The solution may or may not be buffered to a pH from about 5 to about 9, with more preferred pH's being from about 6 to about 7.5. These concentrations of hydrogen peroxide can be diluted in water or in an aqueous solution of about 2% to about 50% by volume of alcohol, most preferably ethanol. For additional information concerning preferred peroxy disinfecting agents useful in certain disinfecting embodiments of the present invention, reference can be made, for example, to U.S. Pat. No. 6,206,931.

In certain embodiments, flowable ECM based fill materials of the present invention can be prepared to have desirable properties for handling and use. For example, fluidized ECM hydrolysates can be prepared in an aqueous medium, which can thereafter be effective to create a gel form fill material. Such prepared aqueous mediums can have any suitable level of ECM hydrolysate therein. Typically, the ECM hydrolysate will be present in the aqueous medium at a concentration of about 2 mg/ml to about 200 mg/ml, more typically about 20 mg/ml to about 200 mg/ml, and in some embodiments about 30 mg/ml to about 120 mg/ml. In certain illustrative forms, the aqueous ECM hydrolysate composition will have an injectable character. Furthermore, flowable ECM compositions can be prepared so that in addition to neutralization, heating to physiologic temperatures (such as 37° C.) will substantially reduce the gelling time of the material.

Turning now to alternative fill material embodiments, the fill material can comprise a suitable solidifying polymer, such as HEMA. Upon addition of a catalyst to HEMA at a certain temperature, HEMA will gradually change from a liquid form to either a gelatinous or solid form over approximately twenty minutes. This change in form is desirable in a fill material because the material can easily flow into the occlusion device, eliminating void space between the device and the vessel wall, and then solidify, thereby enhancing the occlusion ability of the balloon. For more information on HEMA and other fill materials useful in the present invention, reference can be made, for example, to U.S. Pat. Nos. 4,819,637, 5,222,970, 5,304,123, 5,411,475, and/or 5,830,228.

Additionally, the fill material, including, e.g. remodelable ECM fill materials, can include one or more radiopaque and/or ecogenic markers or a radiopaque coating or impregnation to assist in visualization of the material during a non-invasive procedure. For example, radiopaque substances containing tantalum, barium, iodine, or bismuth, e.g. in powder form, can be coated upon or incorporated within a fill material, such that, for example, the location of the fill material within a patient's body can be detected.

Figure 20:
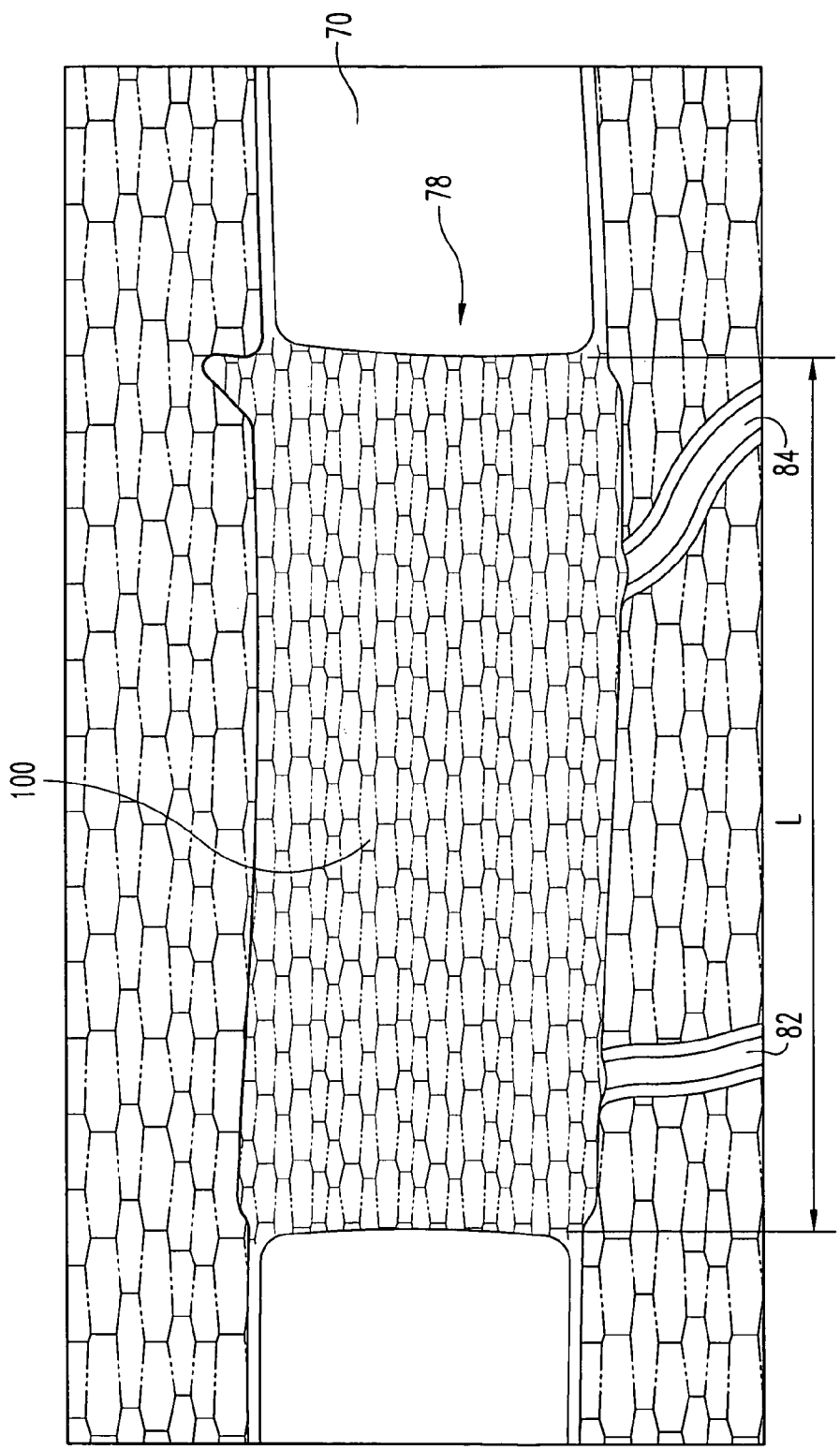
FIG. 20 depicts an illustrative occlusion embodiment of the present invention.

Turning now to FIG. 20, shown is an illustrative occluded vessel 70 after sufficient time to allow a patient's body to remodel a remodelable occlusion device filled with remodelable fill material 78. As can be seen in FIG. 20, patient tissue 100 has substantially invaded and remodeled both the balloon and the fill material, resulting in a vessel 70 that is occluded with a patient's own tissue.

Occlusion devices of the invention will generally be of sufficient dimension to achieve occlusion of the desired stretch of vascular vessel, either alone or in combination with other similar or differing devices. In certain embodiments, the occlusion device will have a length of at least about 10 cm, and in many situations at least about 20 cm. Indeed, for preferred occlusion procedures involving a significant stretch of an artery or vein, occlusion devices having lengths greater than 30 cm can be used. Illustratively, in the occlusion of the GSV in human adolescents or adults, occlusion devices having lengths of at least about 40 cm or 50 cm can be used.

While discussions above focus upon occluding the GSV via access at the knee level, the GSV may also be accessed at a lower level, e.g. near the ankle. During such access, any or all of the GSV occurring between the ankle and the saphenofemoral junction may be subjected to occlusion. Other veins in the leg(s) that may be involved in the varicose vein condition may also be occluded, alternatively or in addition to the GSV. For example, the lesser saphenous vein, or varicose veins themselves, may be occluded and obliterated in accordance with certain embodiments of the invention. Further, other bodily lumens, veins, or arteries, either in the leg(s) or elsewhere in the body, may be occluded within embodiments of the present invention by obtaining access at any suitable location, e.g. the jugular vein.

Percutaneously conducted occlusion procedures of the invention will typically be performed under local anesthesia, such as at the access site. In addition, after completion of the procedure, it may be beneficial to use graduated compression stockings in the occluded area, for example for a week or more. Compression of the occluded area may serve to facilitate permanent closure of the occluded vessel, for example when applied during a remodeling period during which tissue ingrowth into the occluded lumen occurs.

Sheaths, dilators, wire guides, and needles, when used in certain embodiments of the present invention, can all be conventional marketed products or modifications thereof. For example, sheaths can be formed from PTFE (e.g. Teflon) or polyamide (e.g. Nylon) material, or a combination of materials such as an assembly including an inner layer of PTFE, a flat wire coil over the PTFE for kink resistance, and a polyamide (Nylon) outer layer to provide integrity to the overall structure and a smooth surface (e.g. as in the Flexor sheath, Cook, Inc.). Dilators can be made from conventional dilator/catheter type materials such as polyethylene, polyamide, polyurethane or vinyl, or any combination of these materials. Fittings provided for sheath/dilator assemblies can be conventional elements such as luer locks, and the dilator can have a fitting allowing it to be locked to the sheath during insertion and manipulation. Catheters can be made from conventional materials such as polyethylene, polyamide, PTFE, polyurethane, and other materials.

Delivery sheaths used in certain embodiments of the invention will have a lumen diameter sized to allow for the introduction of a suitable inflatable occlusion device to occlude the artery or vein of interest. Illustratively, the inner diameter (ID) of the final delivery sheath can range from about 6 to 8 French up to about 40 French, although other sizes may of course be used to suit a particular patient, technology, or situation.

As is conventional, the distal ends and/or other portions of the catheters, sheaths, dilators, wires, inflatable occlusion devices or other components used in percutaneous procedures can include markers that can be X-ray, sonographically, or otherwise non-invasively visualized to identify their location during the procedure. Metallic bands of stainless steel, tantalum, platinum, gold, or other suitable materials, which include a dimple pattern, can serve for both ultrasound and X-ray identification.

Certain embodiments of the invention can also include medical kits, such as a remodelable balloon inverted within a delivery cannula and a deployment sheath with a compliant tip, sealed within sterile medical packaging. The final, packaged product is provided in a sterile condition. This may be achieved, for example, by gamma, e-beam or other irradiation techniques, ethylene oxide gas, or any other suitable sterilization technique, and the materials and other properties of the medical packaging will be selected accordingly. The prosthesis device may be packaged wet or after it is dried.

In additional aspects, any vein, artery, or other bodily lumen or cavity, such as fallopian tubes, vas deferens, aneurisms, and/or other bodily ducts or other arterial or venous malformations may be occluded within embodiments of the present invention by obtaining access at any suitable location, such as the jugular vein or otherwise.

All publications cited herein are hereby incorporated by reference in their entirety as if each had been individually incorporated by reference and fully set forth. In addition, U.S. Provisional Patent Application Ser. No. 60/633,543, filed Dec. 6, 2004 and entitled, "Inflatable Occlusion Devices, Methods, and Systems," as well as its corresponding U.S. Utility patent application Ser. No. 11/294,998, filed Dec. 6, 2005 and entitled, "Inflatable Occlusion Devices, Methods, and Systems," are hereby incorporated herein by reference in their entirety.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for occluding a portion of the vasculature, comprising:
   providing access to the vasculature;
   providing a balloon including a balloon wall formed from a remodelable extracellular matrix layer isolated from a biological tissue source and containing native crosslinks from the biological tissue source, the remodelable extracellular matrix layer being effective upon implantation to induce cellular invasion and ingrowth into the balloon wall so that the balloon wall becomes remodeled with patient tissue, wherein at least a portion of the balloon is inverted;
   providing a cannulated device, wherein a lumen of the cannulated device is in communication with the balloon;
   delivering the balloon and device to a site within the vasculature; and
   locating the balloon in the vasculature after delivery so as to cause occlusion of the vasculature.

2. The method of claim 1, further comprising filling the balloon with a flowable material comprising a remodelable extracellular matrix fill material that is effective to induce cellular invasion and ingrowth following implantation so that the remodelable extracellular matrix fill material becomes remodeled with patient tissue.

3. The method of claim 2, wherein the balloon has a length of at least about 20 cm.

4. The method of claim 1, wherein the remodelable extracellular matrix layer comprises submucosa, dura mater, pericardium, or basement membrane.

5. The method of claim 4, wherein the submucosa comprises mammalian submucosa.

6. The method of claim 5, wherein mammalian submucosa comprises porcine, bovine, or ovine submucosa.

7. The method of claim 6, wherein porcine submucosa comprises adult porcine submucosa.

8. The method of claim 1, wherein the balloon comprises a single wall.

9. The method of claim 8, wherein the balloon has a length of at least about 40 cm.

10. A method for treating a venous dysfunction in a leg of a patient, comprising:
    providing a percutaneous access to a venous vessel;
    providing a cannulated device having a lumen, a proximal end, and a distal end and an inflatable occlusion device having a proximal end and a distal end and including an occlusion device wall that comprises a naturally-derived and non-reconstituted collagenous extracellular matrix material, wherein at least a portion of the inflatable occlusion device is received within the lumen of the cannulated device;
    delivering the cannulated device containing at least a portion of the inflatable occlusion device through the percutaneous access to a site within the venous vessel; and
    passing fill material into the inflatable occlusion device after delivery so as to occlude the venous vessel, wherein the fill material comprises a remodelable extracellular matrix fill material isolated from a biological tissue source and effective to induce cellular invasion and ingrowth following implantation so that the remodelable extracellular matrix fill material becomes remodeled with patient tissue.

11. The method of claim 10, wherein:
    the cannulated device further comprises an inner tube, thereby creating an annular region within the cannulated device; and
    the inflatable occlusion device further comprises an inner wall and an outer wall, wherein the inner wall is connected to the tube and the outer wall is connected to the cannulated device.

12. The method of claim 11, further comprising anchoring the inflatable occlusion device, wherein the anchoring is sufficient to prevent the inflatable occlusion device from migrating from the site.

13. The method of claim 12, wherein said anchoring comprises securing the proximal end of the inflatable occlusion device to a portion of the venous vessel.

14. The method of claim 10, wherein said passing fill material comprises transferring material from a syringe through the cannulated device and into the inflatable occlusion device.

15. The method of claim 14, further comprising sealing the proximal end of the inflatable occlusion device after passing fill material into the inflatable occlusion device.

16. The method of claim 15, wherein sealing comprises tying the proximal end of the inflatable occlusion device with at least one knot.

17. The method of claim 10, wherein the fill material comprises collagen, chitosan, oxidized regenerated cellulose, calcium alginate, alginate, or any suitable combination thereof.

18. The method of claim 10, wherein said occlusion device wall includes a remodelable extracellular matrix layer isolated from a biological tissue source and effective upon implantation to induce cellular invasion and ingrowth into the occlusion device wall so that the wall becomes remodeled with patient tissue.

19. The method of claim 18, wherein the inflatable occlusion device has a length of at least about 20.

20. The method of claim 19, wherein the remodelable extracellular matrix fill material comprises fluidized material.

21. A method for occluding a vascular vessel, comprising:
    providing a cannulated device having a proximal end, a distal end, and a lumen, wherein the lumen is in communication with the interior of an at least partially inverted balloon that includes a balloon wall formed from a remodelable extracellular matrix layer isolated from a biological tissue source and containing native crosslinks from the biological tissue source, said remodelable extracellular matrix layer effective upon implantation to induce cellular invasion and ingrowth into the balloon wall so that the balloon wall becomes remodeled with patient tissue, the balloon having a proximal end and a distal end;
- locating the balloon and cannulated device at a site within the vascular vessel;
- positioning the distal end of the balloon within the vascular vessel after locating the balloon and cannulated device within the vessel; and
- passing fill material into the balloon.

22. The method of claim 21, wherein the distal end of the balloon is positioned in the vessel with a thin walled tube.

23. The method of claim 21, wherein the distal end of the balloon is closed and positioning the closed end of the balloon further comprises passing fill material through the cannulated device so as to deploy the closed end of the balloon from the cannulated device into the vessel.

24. A method for treating a venous dysfunction in a leg of a human, comprising:
- providing a device, the device having a proximal end, a distal end, and a lumen, wherein the device lumen is in communication with an interior of an at least partially inverted fillable member attached to the device, the fillable member further having a proximal end and a distal end and including a wall that comprises a naturally-derived and non-reconstituted collagenous material;
- providing a percutaneous access to a saphenous vein of the leg;
- locating the at least partially inverted member and device within the saphenous vein through the percutaneous access;
- locating the distal end of the finable member in the saphenous vein after locating the member and device within the saphenous vein;
- expanding the member in the saphenous vein by passing a fill material through the device lumen after locating the distal end of the member in the vein, so as to cause occlusion of the saphenous vein; and
- detaching the fillable member from the device.

25. The method of 24, wherein expanding the fillable member occurs on at least two occasions.

26. A method for occluding a portion of the vasculature, comprising:
- locating an inverted balloon within the vasculature, wherein the inverted balloon is in communication with a lumen of a cannulated device, and wherein the inverted balloon has a balloon wall comprising a naturally-derived and non-reconstituted remodelable extracellular matrix layer isolated from a biological tissue source and effective upon implantation to induce cellular invasion and ingrowth into the balloon wall so that the balloon wall becomes remodeled with patient tissue;
- passing fill material through the cannulated device lumen into the balloon after the balloon is located within the vasculature; and
- removing the cannulated device from the vasculature while leaving the balloon within the vasculature.

27. The method of claim 26, further comprising:
- anchoring the balloon, wherein the anchoring is sufficient to prevent the balloon from migrating within the vasculature.

28. The method of claim 27, wherein the balloon has a proximal end and a distal end and said anchoring comprises securing the proximal end of the balloon to a portion of the vasculature.

29. The method of claim 26, wherein said balloon has a length of at least about 10 cm.

30. The method of claim 26, wherein said fill material comprises a remodelable extracellular matrix fill material isolated from a biological tissue source and effective to induce cellular invasion and ingrowth following implantation so that the remodelable extracellular matrix fill material becomes remodeled with patient tissue.

31. The method of claim 30, wherein said balloon has a length of at least about 10 cm.

32. A method for delivering a balloon to a site within a vascular vessel, comprising:
- providing a cannulated device having a proximal end, a distal end, and a lumen and an elongate balloon having a proximal end, a body, and a distal end, wherein the interior of the balloon is in communication with the device lumen, the elongate balloon is at least partially inverted, and the elongate balloon has a balloon wall comprising a remodelable extracellular matrix layer isolated from a biological tissue source and containing native crosslinks from the biological tissue source, said remodelable extracellular matrix layer effective upon implantation to induce cellular invasion and ingrowth into the balloon wall so that the balloon wall becomes remodeled with patient tissue;
- providing access to the vascular vessel;
- locating the cannulated device and the at least partially inverted balloon at the site; and
- deploying the balloon into the vascular vessel.

33. The method of claim 32, further comprising locating the balloon body and the distal end of the balloon within the lumen of the cannulated device before the device is located at the site.

34. The method of claim 33, wherein the balloon body and the distal end of the balloon are located within the lumen of the cannulated device by evacuating the lumen of the cannulated device.

35. The method of claim 33, further comprising folding the balloon in a controlled pattern so as to reduce its packing density.

36. The method of claim 35, wherein the balloon is folded in a saw tooth pattern.

37. A method for increasing the packing density of a balloon, comprising providing a balloon having a balloon wall comprising a naturally-derived and non-reconstituted remodelable extracellular matrix layer isolated from a biological tissue source and effective upon implantation to induce cellular invasion and ingrowth into the balloon wall so that the balloon wall becomes remodeled with patient tissue, and folding the balloon in a controlled fashion, so as to reduce the diameter of a percutaneous balloon delivery system.

38. The method of claim 37, wherein the balloon is folded in a circular saw tooth pattern.

39. The method of claim 38, wherein the balloon comprises small intestine submucosa.

40. A method for treating a vascular vessel, comprising:
- providing a fillable member, wherein at least a portion of said fillable member is in an inverted configuration, and wherein a wall of said fillable member comprises a naturally-derived and non-reconstituted remodelable extracellular matrix material isolated from a biological tissue source and effective upon implantation to induce cellular invasion and ingrowth into the wall so that the wall becomes remodeled with patient tissue;
- providing access to a vascular vessel with a cannulated device, the cannulated device having a proximal end, a distal end, and a lumen;

locating at least a portion of the fillable member within a vascular vessel by passing the member through the lumen.

41. The method of claim 40, also comprising passing a fill material into the fillable member.

42. The method of claim 41, wherein the fill material is passed into the fillable member through a tubular device.

\* \* \* \* \*